(12) United States Patent
Shibata et al.

(10) Patent No.: US 10,918,279 B2
(45) Date of Patent: Feb. 16, 2021

(54) SYSTEM FOR CONNECTING MEDICAL IMAGE CAPTURE APPARATUSES VIA A NETWORK

(71) Applicant: General Electric Company, Schenectady, NY (US)

(72) Inventors: Yuko Shibata, Hino (JP); Seiji Funaya, Hino (JP); Yuri Teraoka, Hino (JP); Masaru Ogasawara, Hino (JP); Manabu Arima, Hino (JP)

(73) Assignee: GE Precision Healthcare LLC, Wauwatosa, WI (US)

( * ) Notice: Subject to any disclaimer, the term of this patent is extended or adjusted under 35 U.S.C. 154(b) by 95 days.

(21) Appl. No.: 16/396,450

(22) Filed: Apr. 26, 2019

(65) Prior Publication Data
US 2019/0328228 A1  Oct. 31, 2019

(51) Int. Cl.
| | | |
|---|---|---|
| A61B 5/00 | (2006.01) | |
| G16H 30/40 | (2018.01) | |
| G16H 30/20 | (2018.01) | |
| G16H 40/20 | (2018.01) | |
| G16H 40/67 | (2018.01) | |
| A61B 8/00 | (2006.01) | |

(52) U.S. Cl.
CPC .......... *A61B 5/0013* (2013.01); *A61B 5/0022* (2013.01); *G16H 30/20* (2018.01); *G16H 30/40* (2018.01); *G16H 40/20* (2018.01); *G16H 40/67* (2018.01); *A61B 8/54* (2013.01); *A61B 8/565* (2013.01); *A61B 8/585* (2013.01)

(58) Field of Classification Search
CPC ....... A61B 5/0013; A61B 5/0022; A61B 8/54; A61B 8/565; A61B 8/585; G16H 30/20; G16H 30/40; G16H 40/20; G16H 40/67
See application file for complete search history.

(56) References Cited

U.S. PATENT DOCUMENTS

| | | | | |
|---|---|---|---|---|
| 6,464,636 | B1 * | 10/2002 | Kinicki .................. | A61B 8/00 600/437 |
| 9,218,452 | B2 * | 12/2015 | Varna ..................... | G16H 10/60 |
| 10,592,691 | B2 * | 3/2020 | Holl ....................... | H04L 67/141 |
| 2005/0043620 | A1 * | 2/2005 | Fallows ................. | A61B 8/565 600/437 |

(Continued)

FOREIGN PATENT DOCUMENTS

| | | |
|---|---|---|
| JP | 2014-193193 A | 10/2014 |
| JP | 2015-229069 A | 12/2015 |

(Continued)

*Primary Examiner* — Thomas J Dailey

(57) ABSTRACT

A system comprises a plurality of ultrasonic diagnostic apparatuses connected via a network, and comprises: a storage device in which specification information for specifying some of preferences A, B, C to be shared between first and second ultrasonic diagnostic apparatuses is stored; and at least one control device. The control device executes a deciding function of deciding, once the first ultrasonic diagnostic apparatus has accepted an input of a value of at least any one of the plurality of preferences A, B, C, whether or not a preference corresponding to the input value is the preference to be shared based on said specification information, and sets the value of the preference into the second ultrasonic diagnostic apparatus.

19 Claims, 17 Drawing Sheets

(56) References Cited

U.S. PATENT DOCUMENTS

| | | | |
|---|---|---|---|
| 2006/0173713 A1* | 8/2006 | Petro | G16H 40/20 705/2 |
| 2011/0293152 A1* | 12/2011 | Choi | A61B 8/585 382/128 |
| 2014/0121489 A1* | 5/2014 | Kommu Chs | A61B 8/4427 600/407 |
| 2019/0039078 A1 | 2/2019 | Chuman | |

FOREIGN PATENT DOCUMENTS

| | | |
|---|---|---|
| JP | 2016-22096 A | 2/2016 |
| JP | 2017-111471 A | 6/2017 |
| WO | 2012/096109 W | 7/2012 |
| WO | 2015/182478 W | 12/2015 |

* cited by examiner

|  | PREF A | PREF B | PREF C |
|---|---|---|---|
| ULTRASONIC DIAGNOSTIC APPARATUS 101 |  | SHARED |  |
| ULTRASONIC DIAGNOSTIC APPARATUS 102 | SHARED | SHARED |  |
| ULTRASONIC DIAGNOSTIC APPARATUS 103 | SHARED |  |  |

|  | PREF A | PREF B | PREF C |
|---|---|---|---|
| ULTRASONIC DIAGNOSTIC APPARATUS 101 |  | SHARED |  |

|  | PREF A | PREF B | PREF C |
|---|---|---|---|
| ULTRASONIC DIAGNOSTIC APPARATUS 102 | SHARED | SHARED |  |

|  | PREF A | PREF B | PREF C |
|---|---|---|---|
| ULTRASONIC DIAGNOSTIC APPARATUS 103 | SHARED |  |  |

I3

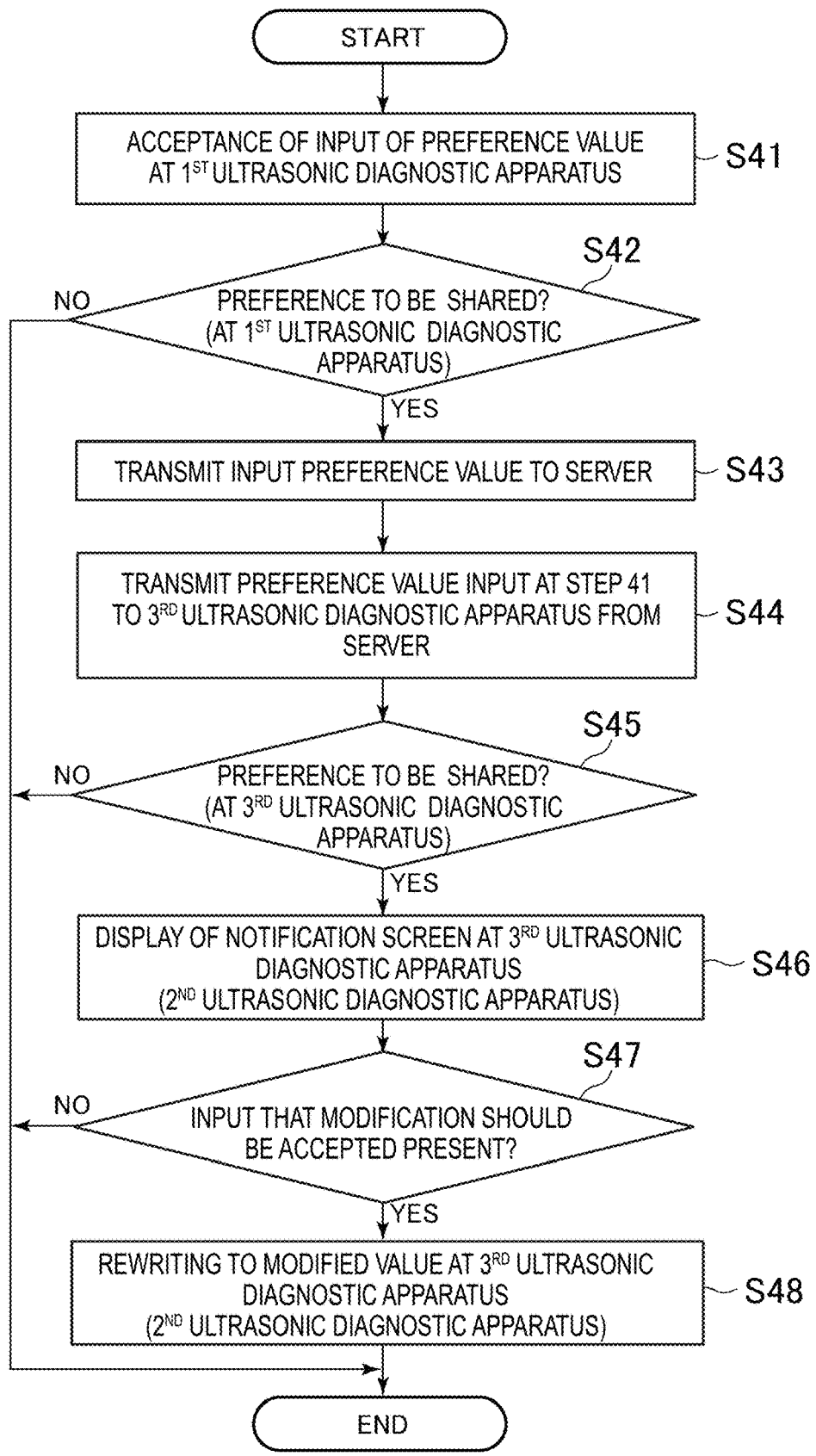

SYSTEM FOR CONNECTING MEDICAL IMAGE CAPTURE APPARATUSES VIA A NETWORK

FIELD OF THE INVENTION

The present invention relates to a system in which medical image capture apparatuses are connected via a network.

BACKGROUND OF THE INVENTION

A medical image capture apparatus has a large number of preferences to be set therein. For example, an ultrasonic diagnostic apparatus, which is an example of medical image capture apparatuses, has such preferences including several kinds of imaging conditions for acquiring an ultrasonic image, a body pattern, a comment, a cursor for performing measurement, conditions of image reconstruction for obtaining a 3D image or the like (see Patent Documents 1 and 2, for example).

BRIEF DESCRIPTION OF THE INVENTION

The invention, in one aspect, made for solving the aforementioned problems is a system comprising a plurality of medical image capture apparatuses each having an input device for accepting an input by an operator, said plurality of medical image capture apparatuses being connected via a network, and including a first medical image capture apparatus and a second medical image capture apparatus sharing between them some of a plurality of preferences set in each of said plurality of medical image capture apparatuses, said system comprising: a storage device in which specification information is stored, said specification information specifying some of the plurality of preferences set in each of said plurality of medical image capture apparatuses that are to be shared between said first and second medical image capture apparatuses; and at least one control device, said control device executing: a deciding function of deciding, once said input device in said first medical image capture apparatus has accepted an input of a value of at least any one of said plurality of preferences, whether or not a preference corresponding to said input value is the preference to be shared between said first and second medical image capture apparatuses based on said specification information; and a setting function of setting, in a case that said preference is decided by said deciding function to be the preference to be shared, the value of said preference input at said input device into said second medical image capture apparatus.

The invention, in another aspect, is a system comprising a plurality of medical image capture apparatuses connected with one another via a network, wherein at least some of said plurality of medical image capture apparatuses include a first medical image capture apparatus and a second medical image capture apparatus sharing between them values of at least some of a plurality of preferences set in each of said medical image capture apparatuses, said first medical image capture apparatus has a first storage device, a first input device, and a first control device, said second medical image capture apparatus has a second storage device and a display device, in said first and second storage devices are stored the values of said preferences to be shared, said first input device is configured to accept an input for modifying the value of said preference to be shared stored in said storage device in said first medical image capture apparatus, said first control device is configured to execute, once said first input device has accepted the input for modifying the value of said preference, a first transmitting function of transmitting the input modified value to said network, said display device is configured to display, during capture of a medical image in said second medical image capture apparatus, a notification window for notifying the preference to which said modified value input to said second medical image capture apparatus after being transmitted to said network pertains, and said preference is classified into a category that makes it possible to decide whether or not said modified value affects the capture of said medical image.

BRIEF DESCRIPTION OF THE DRAWINGS

FIG. 9 A conceptual diagram showing an example of the specification information in the variation of the first embodiment.

FIG. 10 A conceptual diagram showing another example of the specification information in the variation of the first embodiment.

FIG. 11 A conceptual diagram showing another example of the specification information in the variation of the first embodiment.

FIG. 19 A flow chart showing an operation of the second variation of the second embodiment.

DETAILED DESCRIPTION OF THE INVENTION

Figure 1:
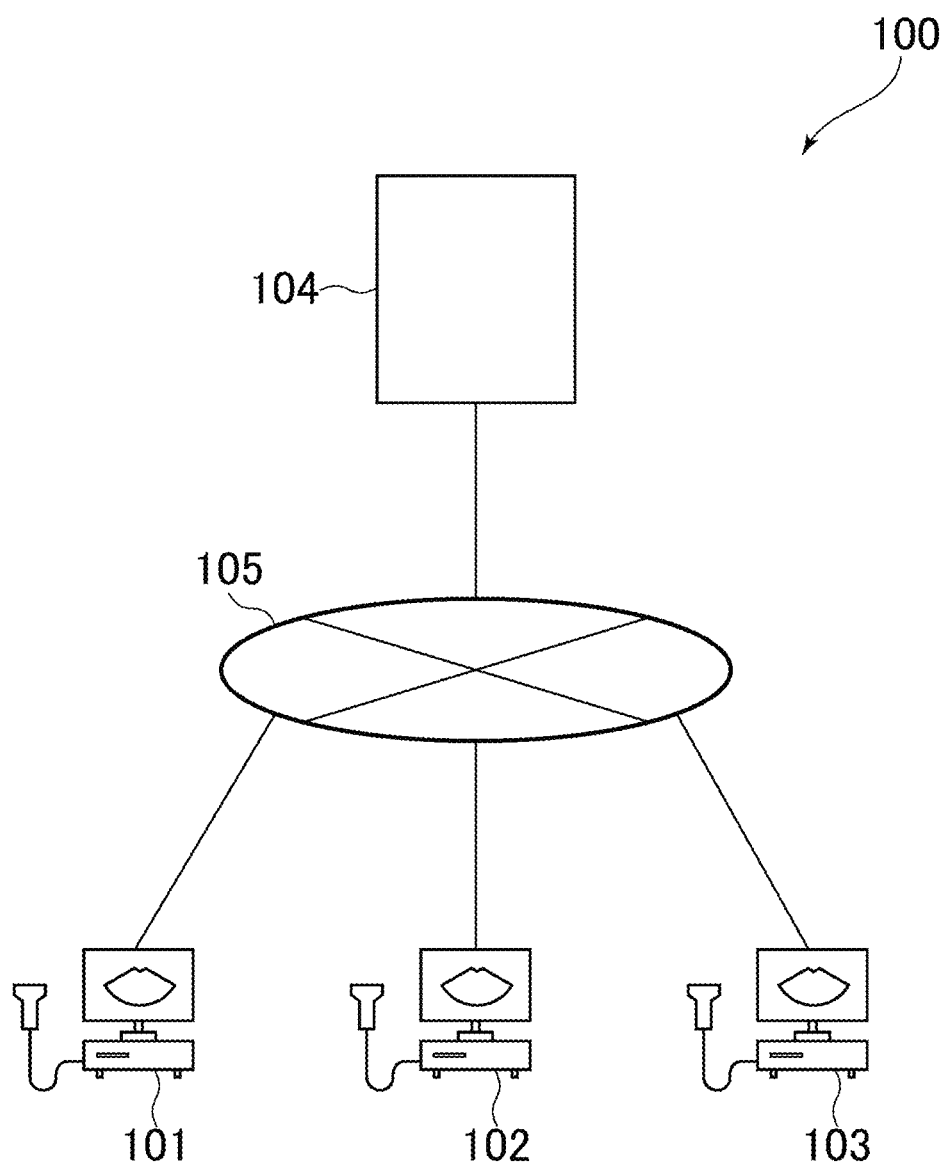
FIG. 1 A block diagram showing the overall configuration of a system in embodiments of the present invention.

According to the invention in the one aspect described above, specification information specifying some of the plurality of preferences set in each of said plurality of medical image capture apparatuses that are to be shared between said first and second medical image capture apparatuses is stored. Then, once said input device in said first medical image capture apparatus has accepted an input of a value of a preference, said deciding function decides whether or not a preference corresponding to said input value is the preference to be shared between said first and second medical image capture apparatuses based on said specification information. In the case that said preference is decided to be the preference to be shared, said setting function sets the value of said preference input at said input device into said second medical image capture apparatus. Sharing of values of some of preferences can thus be easily achieved.

According to the invention in the other aspect described above, when an input of modifying the value of said preference is performed at said first medical image capture apparatus, said notification window is displayed in said second medical image capture apparatus. Said notification window is for notifying a category to which the modified value pertains, where the category makes it possible to decide whether or not said preference of said modified value affects the image capture; therefore, by the operator of said second medical image capture apparatus confirming said notification window, (s)he can decide whether or not the modified value input at said first medical image capture apparatus should be stored in said second medical image capture apparatus. Therefore, the modified value input at said first medical image capture apparatus can be set into said second medical image capture apparatus without interfering with the image capture at said second medical image capture apparatus or missing the event that an input has been performed at said first medical image capture apparatus.

In most cases, the preferences described above are customized according to the user's purpose and/or preference. In a hospital having a plurality of ultrasonic diagnostic apparatuses, however, there is a need to share values of the preferences for guaranteeing precision of examinations.

On the other hand, especially in the case that ultrasonic diagnostic apparatuses are possessed across a plurality of departments in a hospital, rather than sharing values of all preferences among all the ultrasonic diagnostic apparatuses, it is sometimes preferable to set some of the preferences with values specific to each department. In this case, values of only some of the plurality of preferences in a certain ultrasonic diagnostic apparatus are to be shared with those in another ultrasonic diagnostic apparatus. When thus attempting to share values of some of preferences, an only conventionally available technique is to manually set such values again in every apparatus, which is cumbersome.

Moreover, in the case that values of preferences are shared among a plurality of ultrasonic diagnostic apparatuses, and when a value of a preference is modified in any of the plurality of ultrasonic diagnostic apparatuses, the modification should be reflected in other ultrasonic diagnostic apparatuses as well. Accordingly, it may be contemplated to transmit the modified value from the ultrasonic diagnostic apparatus at which the modification has been made to another ultrasonic diagnostic apparatus, and set the modified value there. However, when image capture is running in the other ultrasonic diagnostic apparatus, and in the case that the modified value relates to the current image capture, immediate setting of the modified value may interfere with the examination. For example, in the case that the modified value is such a value that affects image quality of an image currently captured in the other ultrasonic diagnostic apparatus, modification on a setting of image quality or the like during the image capture may confuse an operator and interfere with the examination.

Now several embodiments of the present invention will be described referring to the accompanying drawings. In the following embodiments, the medical image capture apparatus in the present invention is exemplified by an ultrasonic diagnostic apparatus.

To begin with, a first embodiment will be described. A system 100 shown in FIG. 1 comprises a plurality of ultrasonic diagnostic apparatuses 101, 102, 103, and a server 104. The plurality of ultrasonic diagnostic apparatuses 101, 102, 103 are connected with one another via a network 105. The plurality of ultrasonic diagnostic apparatuses 101, 102, 103 are also each connected with the server 104 via the network 105.

Figure 2:
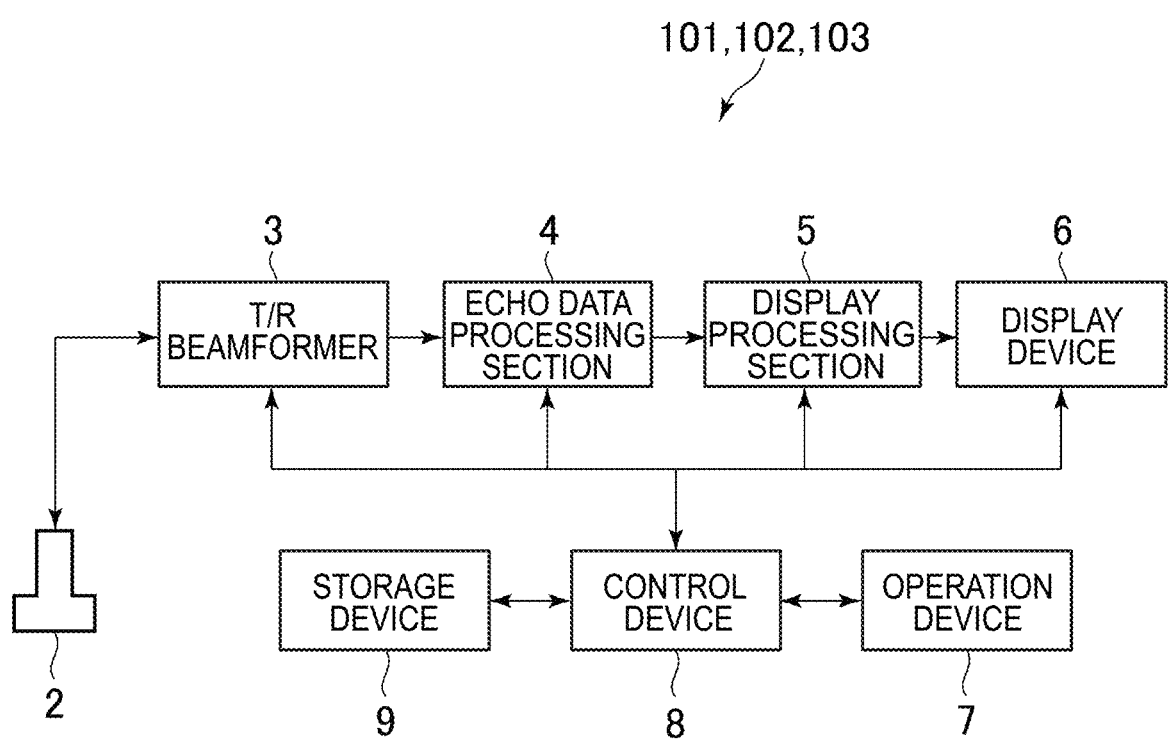
FIG. 2 A block diagram showing a configuration of an ultrasonic diagnostic apparatus constituting the system shown in FIG. 1.

As shown in FIG. 2, the ultrasonic diagnostic apparatuses 101, 102, 103 each comprise an ultrasonic probe 2, a transmission/reception (T/R) beamformer 3, an echo data processing section 4, a display processing section 5, a display device 6, an input device 7, a control device 8, and a storage device 9.

The ultrasonic probe 2 transmits ultrasound and receives its echo signals to/from a biological tissue in a subject to be examined. The T/R beamformer 3 drives the ultrasonic probe 2 to transmit ultrasound having predetermined transmission conditions based on control signals from the control device 8. The T/R beamformer 3 also applies signal processing, such as phased addition processing, to echo signals of the ultrasound.

The echo data processing section 4 applies processing for producing an ultrasonic image to echo data output from the T/R beamformer 3. For example, the echo data processing section 4 applies B-mode processing including logarithm compression processing, envelope detection processing, etc. to create B-mode data.

The display processing section 5 scan-converts raw data from the echo data processing section 4 by a scan converter to create image data. The display processing section 5 scan-converts the B-mode data, for example, to create B-mode image data. The display processing section 5 also causes an ultrasonic image based on the image data to be displayed on the display device 6. The display processing section 5 causes, for example, a B-mode image based on the B-mode image data to be displayed on the display device 6.

The display device 6 is an LCD (Liquid Crystal Display), an organic EL (Electro-Luminescence) display or the like.

The input device 7 is a device for accepting user's inputs of commands and information. The input device 7 is configured to comprise buttons and a keyboard for accepting operator's inputs of commands and information, and to further comprise a pointing device, such as a trackball.

The control device 8 is circuitry for controlling the ultrasonic diagnostic apparatus 1, and is a processor, such as, for example, a CPU (Central Processing Unit). The control device 8 loads programs stored in the storage device 9 to control several sections in the ultrasonic diagnostic apparatus 1. The control device 9 is an exemplary embodiment of the control device in the present invention.

For example, the control device 8 loads programs stored in the storage device 9, and causes the functions of the T/R beamformer 3, echo data processing section 4, and display processing section 5 described above to be executed according to the loaded programs. The control device 8 may execute all of the functions of the T/R beamformer 3, all of the functions of the echo data processing section 4, and all of the functions of the display processing section 5 according to the programs, or may execute only some of the functions according to the programs. In the case that only some of the functions are executed according to the programs, the rest of the functions may be executed by hardware such as circuitry.

The control device 8 may also execute functions other than those of the T/R beamformer 3, echo data processing section 4, and display processing section 5 according to programs stored in the storage device 8. This will be discussed in detail later.

The storage device 9 includes non-transitory storage media and transitory storage media. The non-transitory storage media are non-volatile storage media such as, for example, HDD (Hard Disk Drive) and ROM (Read Only Memory). The non-transitory storage media may include portable storage media such as CDs (Compact Disks) and DVDs (Digital Versatile Disks). Programs to be executed by the control device 8 are stored in non-transitory storage media.

The transitory storage media are volatile storage media, such as RAM (Random Access Memory).

In each of the plurality of ultrasonic diagnostic apparatuses 101, 102, 103, a plurality of preferences are set. The preferences are information used in operations of each of the plurality of ultrasonic diagnostic apparatuses 101, 102, 103. Specifically, the preferences include, in each of the plurality of ultrasonic diagnostic apparatuses 101, 102, 103, imaging conditions for acquiring an ultrasonic image, information given to the ultrasonic image, information used for performing measurement in the ultrasonic image, and reconstruction conditions for performing image reconstruction based on data of the ultrasonic image. Note that the preferences are not limited thereto.

The imaging conditions include, for example, a gain value, a focal point depth, filter coefficients, and a contrast value. The imaging conditions may be set for each of a plurality of body parts in the subject. In this case, imaging conditions for each of the plurality of body parts constitute a respective different preference.

The information given to an ultrasonic image includes, for example, a comment provided to the ultrasonic image, and a body pattern. The information used for performing measurement in the ultrasonic image include, for example, a cursor displayed on the ultrasonic image for performing measurement, and a calculation formula. The reconstruction conditions for performing image reconstruction based on data of the ultrasonic images include, for example, reconstruction conditions for producing a 3D or 4D image.

Figure 3:
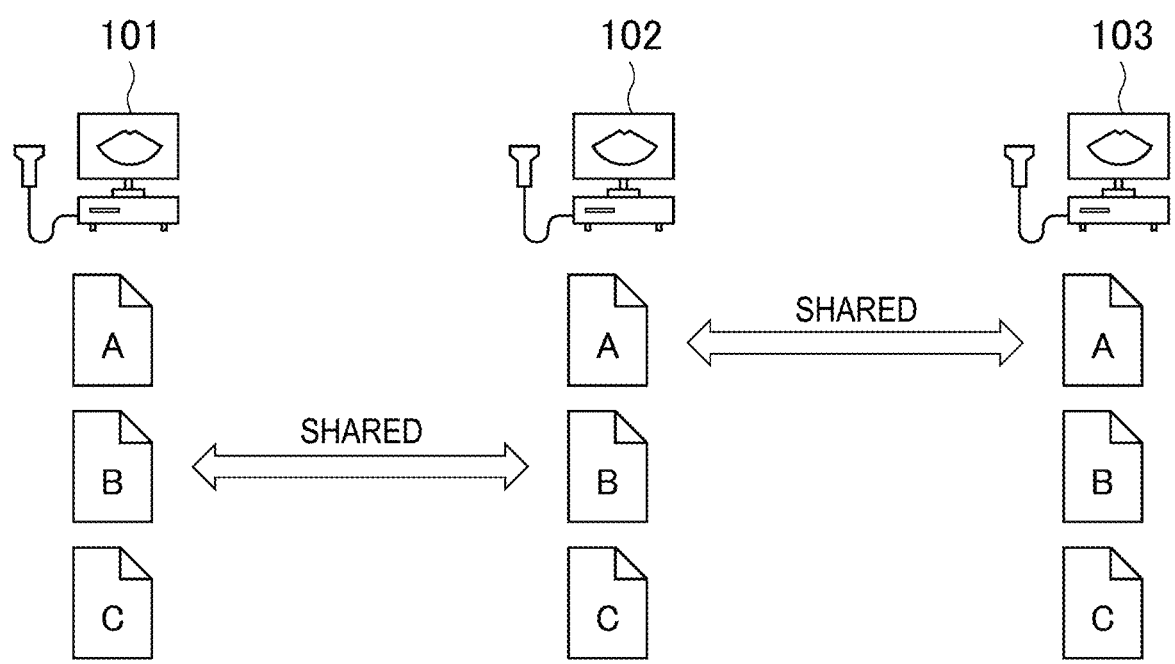
FIG. 3 A diagram explaining preferences set in each of a plurality of ultrasonic diagnostic apparatuses.

For example, as shown in FIG. 3, preferences A, B, C are set in the plurality of ultrasonic diagnostic apparatuses 101, 102, 103. For example, preferences A, B, C are any ones of the aforementioned preferences. The number of preferences is merely exemplary, and a larger number of preferences may be set in practice.

Figure 4:
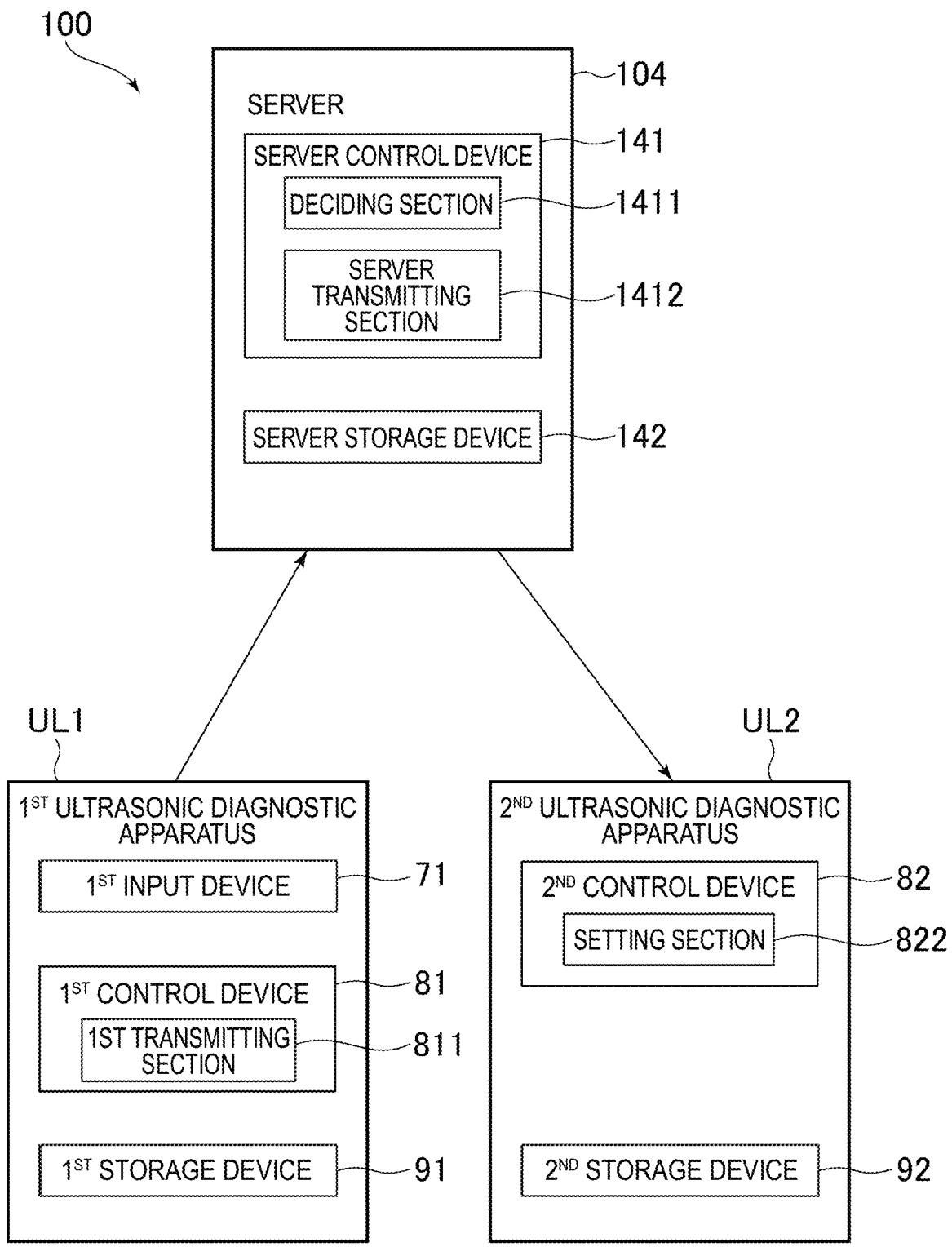
FIG. 4 A block diagram showing a first ultrasonic diagnostic apparatus, a second ultrasonic diagnostic apparatus, and a server.

Of the plurality of ultrasonic diagnostic apparatuses 101, 102, 103, those sharing among them some of the plurality of preferences are referred to herein as a first ultrasonic diagnostic apparatus UL1 and a second ultrasonic diagnostic apparatus UL2. In FIG. 4 are shown the first ultrasonic diagnostic apparatus UL1 and second ultrasonic diagnostic apparatus UL2. The first ultrasonic diagnostic apparatus UL1 is one of the plurality of ultrasonic diagnostic apparatuses 101, 102, 103 at which apparatus an input of a value of a preference is performed. The second ultrasonic diagnostic apparatus UL2 is one of the plurality of ultrasonic diagnostic apparatuses 101, 102, 103 into which apparatus the value of the preference input at the first ultrasonic diagnostic apparatus UL1 is set.

For example, as shown in FIG. 3, the ultrasonic diagnostic apparatuses 101, 102 share a preference B between them. In this case, one of the ultrasonic diagnostic apparatuses 101, 102 constitutes the first ultrasonic diagnostic apparatus UL1, and the other constitutes the second ultrasonic diagnostic apparatus UL2.

The ultrasonic diagnostic apparatuses 102, 103 share a preference A between them. In this case, one of the ultrasonic diagnostic apparatuses 102, 103 constitutes the first ultrasonic diagnostic apparatus UL1, and the other constitutes the second ultrasonic diagnostic apparatus UL2.

As shown in FIG. 4, the input device 7, control device 8, and storage device 9 in the first ultrasonic diagnostic apparatus UL1 are designated herein as a first input device 71, a first control device 81, and a first storage device 91, respectively. The control device 8 and storage device 9 in the second ultrasonic diagnostic apparatus UL2 are designated herein as a second control device 82 and a second storage device 92, respectively, as shown in FIG. 3.

The first input device 71 is an exemplary embodiment of the input device in the present invention. The first control device 81 loads a program stored in the first storage device 91, and causes the function of the first transmitting section 811 to be executed according to the program. The function of the first transmitting section 811 will be discussed later. The function of the first transmitting section 811 is an exemplary embodiment of the first transmitting function in the present invention. The first control device 81 is an exemplary embodiment of the first control device in the present invention.

The second control device 82 loads a program stored in the second storage device 92, and causes the function of the setting section 822 to be executed according to the program. The function of the setting section 822 will be discussed later. The function of the setting section 822 is an exemplary embodiment of the setting function in the present invention. The second control device 82 is an exemplary embodiment of the second control device in the present invention.

The values of the preferences input at the first ultrasonic diagnostic apparatus UL1 are input to the server 104 via the network 105 (not shown in FIG. 3), and are input from the server 104 to the second ultrasonic diagnostic apparatus UL2 via the network 105.

The server 104 has a server control device 141 and a server storage device 142. The server control device 141 loads programs stored in the server storage device 142, and causes the functions of a deciding section 1411 and a server transmitting section 1412 to be executed according to the programs. The functions of the deciding section 1411 and server transmitting section 1412 will be discussed later. The server control device 141 is an exemplary embodiment of the control device and server control device in the present invention. The function of the deciding section 1411 is an exemplary embodiment of the deciding function in the present invention. The function of the server transmitting section 1412 is an exemplary embodiment of the transmitting function in the present invention. The server storage device 142 is an exemplary embodiment of the storage device in the present invention.

Figure 5:
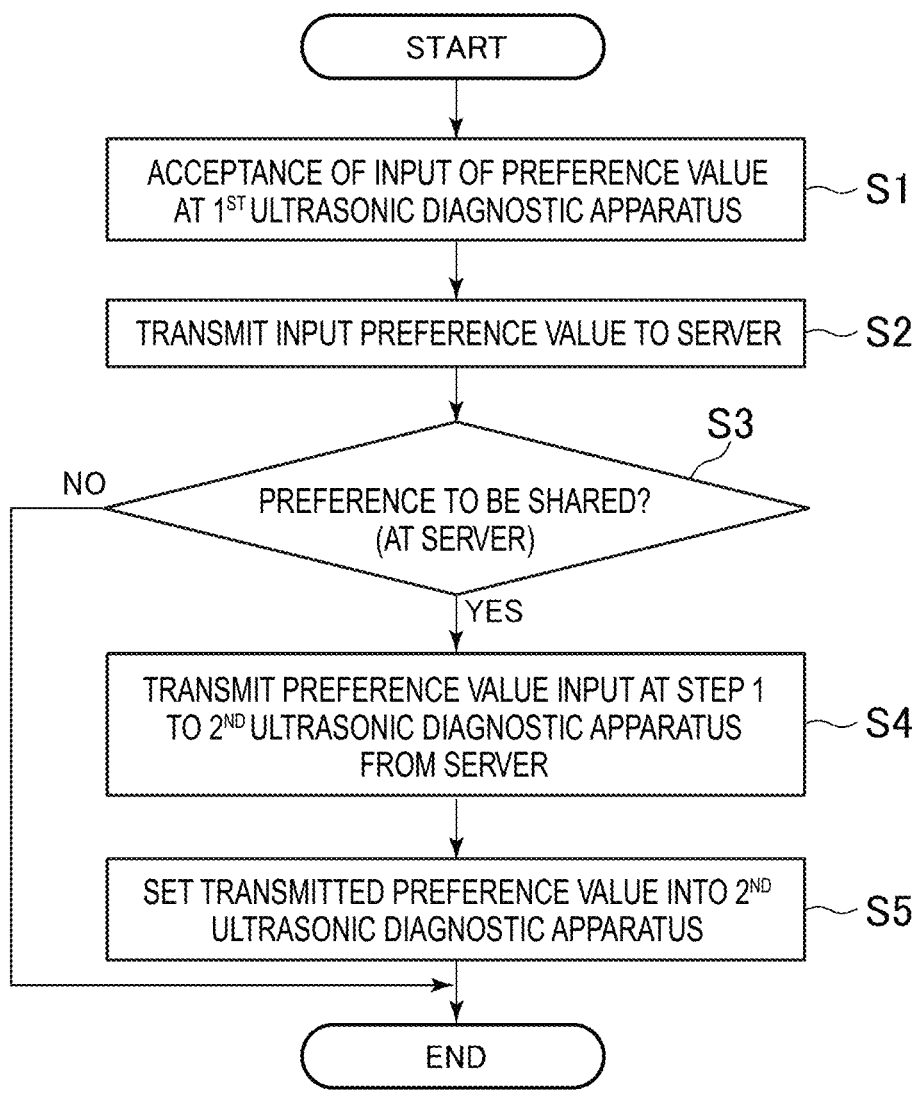
FIG. 5 A flow chart showing an operation of a first embodiment.

Next, an operation of the present embodiment will be described based on the flow chart in FIG. 5. The flow chart in FIG. 5 represents a flow showing processing in setting values of preferences input at the first ultrasonic diagnostic apparatus UL1 as values of the preferences in the second ultrasonic diagnostic apparatus UL2. The flow chart in FIG.

5 includes two cases: one being a case in which the same value has not been set for a preference to be shared between the first ultrasonic diagnostic apparatus UL1 and second ultrasonic diagnostic apparatus UL2 and the same value is set for the first time; the other being a case in which the same value is already set for a preference to be shared between the first ultrasonic diagnostic apparatus UL1 and second ultrasonic diagnostic apparatus UL2 but the value should be modified.

First, at Step S1, the first input device 71 in the first ultrasonic diagnostic apparatus UL1 accepts an operator's input of values of preferences. For example, the first input device 71 accepts an input of values of specific imaging conditions, a comment, a body pattern, image reconstruction conditions, etc., as the values of the preferences. The values input at Step S1 are stored in the first storage device 91.

Next, at Step S2, the first transmitting section 811 transmits the values of the preferences input at Step S1 to the server 104 via the network 105. The first transmitting section 811 transmits the values of said preferences to said server 104 together with identification information that identifies the one (corresponding to the first ultrasonic diagnostic apparatus UL1) of the plurality of ultrasonic diagnostic apparatuses 101, 102, 103 at which apparatus the input of the values of the preferences was performed at Step S1. Alternatively, the values of said preferences may be transmitted together with attribute information that indicates preferences corresponding to the values.

Next, at Step S3, the values of the preferences transmitted at Step S2 are input to the server 104, and the deciding section 1411 decides whether or not a preference corresponding to each value is the preference to be shared between the first ultrasonic diagnostic apparatus UL1 and second ultrasonic diagnostic apparatus UL2. The deciding section 1411 makes said decision based on specification information I shown in FIG. 6. Upon said decision, said preference may alternatively be specified based on said attribute information.

Figure 6:
FIG. 6 A conceptual diagram showing an example of specification information.

The specification information I is stored in the server storage device 142. An example of the specification information I is shown in FIG. 6. The specification information I is for specifying some of the plurality of preferences set in each of the plurality of ultrasonic diagnostic apparatuses 101, 102, 103 that are to be shared between the first ultrasonic diagnostic apparatus UL1 and said second ultrasonic diagnostic apparatus UL2. In the present embodiment, the specification information I specifies preferences to be shared between the first ultrasonic diagnostic apparatus UL1 and second ultrasonic diagnostic apparatus UL2 for each of the plurality of ultrasonic diagnostic apparatuses 101, 102, 103. In other words, the specification information I specifies preferences to be shared between the first ultrasonic diagnostic apparatus UL1 and second ultrasonic diagnostic apparatus UL2 for all the ultrasonic diagnostic apparatuses 101, 102, 103.

The preferences denoted as "SHARED" in the specification information I shown in FIG. 6 are preferences to be shared between the first ultrasonic diagnostic apparatus UL1 and second ultrasonic diagnostic apparatus UL2. Specifically, for the ultrasonic diagnostic apparatus 101, preference B is specified as the preference to be shared with the other ultrasonic diagnostic apparatuses 102, 103. For the ultrasonic diagnostic apparatus 102, preferences A, B are specified as the preferences to be shared with the other ultrasonic diagnostic apparatuses 101, 103. For the ultrasonic diagnostic apparatus 103, preference A is specified as the preference to be shared with the other ultrasonic diagnostic apparatuses 101, 102. Here, the "other ultrasonic diagnostic apparatus" is the first ultrasonic diagnostic apparatus UL1 or second ultrasonic diagnostic apparatus UL2. In other words, the specification information I specifies for each of the plurality of ultrasonic diagnostic apparatuses 101, 102, 103 preferences to be shared with and not to be shared with other ultrasonic diagnostic apparatuses.

For the preference corresponding to the value input at the first input device 71 at Step S1, when both the first ultrasonic diagnostic apparatus UL1 and second ultrasonic diagnostic apparatus UL2 have entries "SHARED" for the preference in the specification information I, the deciding section 1411 decides that it is a preference to be shared between the first ultrasonic diagnostic apparatus UL1 and second ultrasonic diagnostic apparatus UL2. More specifically, the deciding section 1411 identifies which of the plurality of ultrasonic diagnostic apparatuses 101, 102, 103 serves as the first ultrasonic diagnostic apparatus UL1 based on the identification information transmitted from the first transmitting section 811 at Step S2. The deciding section 1411 then decides, for the identified first ultrasonic diagnostic apparatus UL1, whether or not the preference corresponding to the value input at Step S1 is indicated as "SHARED" in the specification information I. The deciding section 1411 moreover decides, for ultrasonic diagnostic apparatuses other than the one of the ultrasonic diagnostic apparatuses 101, 102, 103 that is specified as the first ultrasonic diagnostic apparatus UL1, whether or not the preference corresponding to the value input at Step S1 is indicated as "SHARED" in the specification information I. The deciding section 1411 then identifies the ultrasonic diagnostic apparatus having the entry "SHARED" as the second ultrasonic diagnostic apparatus UL2.

For example, in the case that the input device 7 in the ultrasonic diagnostic apparatus 101 has accepted an input of a value of preference A at Step S1, that is, in the case that the input device 7 in the ultrasonic diagnostic apparatus 101 is the first input device 71 and the value of the input at the first input device 71 is the value of preference A, the deciding section 1411 decides, at Step S3, that preference A is not the preference to be shared between the first ultrasonic diagnostic apparatus UL1 and second ultrasonic diagnostic apparatus UL2. This is because the ultrasonic diagnostic apparatus 101 serving as the first ultrasonic diagnostic apparatus UL1 here does not have an entry "SHARED" for preference A in the specification information I.

On the other hand, in the case that the input device 7 in the ultrasonic diagnostic apparatus 101 has accepted an input of a value of preference B at Step S1, the deciding section 1411 decides, at Step S3, that preference B is the preference to be shared between the first ultrasonic diagnostic apparatus UL1 and second ultrasonic diagnostic apparatus UL2 based on the specification information I. This is because, in the specification information I, the ultrasonic diagnostic apparatus 101 serving as the first ultrasonic diagnostic apparatus UL1 here has an entry "SHARED" for preference B, and at the same time, the ultrasonic diagnostic apparatus 102 corresponding to the second ultrasonic diagnostic apparatus UL2 has an entry "SHARED" for preference B. Since the ultrasonic diagnostic apparatus 102 is an apparatus different from the ultrasonic diagnostic apparatus 101 that has accepted the input of the value of the preference, it corresponds to the second ultrasonic diagnostic apparatus UL2.

The decision by the deciding section 1411 described above based on the specification information I includes identification of the second ultrasonic diagnostic apparatus UL2 with which the preference corresponding to the value input at Step S1 is to be shared. The deciding section 1411 performs identification of the second ultrasonic diagnostic apparatus UL2 based on the specification information I. For example, in the case that the input device 7 in the ultrasonic diagnostic apparatus 101 has accepted an input of a value of preference B at Step S1, the deciding section 1411 identifies the ultrasonic diagnostic apparatus 102 as the second ultrasonic diagnostic apparatus UL2.

In the case that the deciding section 1411 decides that the preference corresponding to the value input at Step S1 is not the preference to be shared between the first ultrasonic diagnostic apparatus UL1 and second ultrasonic diagnostic apparatus UL2 ("NO" at Step S3), the processing is terminated. On the other hand, in the case that the deciding section 1411 decides that the the preference corresponding to the value input at Step S1 is the preference to be shared between the first ultrasonic diagnostic apparatus UL1 and second ultrasonic diagnostic apparatus UL2 ("YES" at Step S3), the flow goes to Step S4.

At Step S4, the server transmitting section 1412 transmits via the network 105 the value of the preference input at Step S1 to the second ultrasonic diagnostic apparatus UL2 identified at Step S3. For example, in the case that the ultrasonic diagnostic apparatus 102 is identified as the second ultrasonic diagnostic apparatus UL2 as described above, the server transmitting section 1412 transmits the value of preference B to the ultrasonic diagnostic apparatus 102.

Next, at Step S5, the setting section 82 in the second ultrasonic diagnostic apparatus UL2 sets the values of the preferences transmitted from the server 104 into the second ultrasonic diagnostic apparatus UL2. Specifically, the setting section 82 stores the values of the preferences transmitted from the server 104 in the second storage device 92. Here, in the case that, for the preference to be shared between the first ultrasonic diagnostic apparatus UL1 and second ultrasonic diagnostic apparatus UL2, the same value has been stored for the same preference in both the first storage device 91 and second storage device 92 before the input at Step S1 is performed, the setting section 82 replaces the value stored in the second storage device 92 with that transmitted from the server 104. For example, the setting section 82 replaces the value of preference B stored in the second storage device 92 with the value of preference B transmitted from the server 104.

On the other hand, in the case that the same value is set for the first time for the preference to be shared between the first ultrasonic diagnostic apparatus UL1 and second ultrasonic diagnostic apparatus UL2, the setting section 82 newly stores the value transmitted from the server 104 in the second storage device 92.

According to the system 100 in the present embodiment, the specification information I is stored in the server storage device 142. The specification information I is for specifying some of the plurality of preferences to be set into each of the plurality of ultrasonic diagnostic apparatuses 101, 102, 103 that are to be shared between the first ultrasonic diagnostic apparatus UL1 and second ultrasonic diagnostic apparatus UL2. Using the specification information I, the processing according to the flow chart in FIG. 5 described above is executed, and preferences are shared between the first ultrasonic diagnostic apparatus UL1 and second ultrasonic diagnostic apparatus UL2; thus, sharing of values of some of the plurality of preferences set in each of the plurality of ultrasonic diagnostic apparatuses 101, 102, 103 can be easily achieved.

As such, preferences whose values are shared among a plurality of ultrasonic diagnostic apparatuses can be used in similar ways in any of the ultrasonic diagnostic apparatuses, which is convenient for the operator. For example, when imaging conditions are to be shared, ultrasonic images can be acquired with identical imaging conditions without tuning the imaging conditions. Likewise, a comment, a body pattern, and further, a cursor for performing measurement and a calculation formula as well may be shared among the plurality of ultrasonic diagnostic apparatuses, whereby they can be used in similar ways without newly creating them in every ultrasonic diagnostic apparatus.

On the other hand, since sharing of values of some of preferences is contemplated according to the present embodiment, a separate value may be set for a preference whose value is desired to be different in a certain ultrasonic diagnostic apparatus from that in another ultrasonic diagnostic apparatus. Thus, the present embodiment enables easy setting of preferences whose values are desired to be shared between the first ultrasonic diagnostic apparatus UL1 and second ultrasonic diagnostic apparatus UL2 while thus keeping preferences having separate values intact.

It should be noted that the same value is not necessarily set for a preference to be shared between the first ultrasonic diagnostic apparatus UL1 and second ultrasonic diagnostic apparatus UL2. For example, when a value of a certain preference is input at the first ultrasonic diagnostic apparatus UL1, the operator of the second ultrasonic diagnostic apparatus UL2 has the option of not setting into the second ultrasonic diagnostic apparatus UL2 the value input at the first ultrasonic diagnostic apparatus UL1. This case results in a condition in which non-identical values are set for the preference to be shared between the first ultrasonic diagnostic apparatus UL1 and second ultrasonic diagnostic apparatus UL2. In this condition, when a value of the certain preference is input again at the first ultrasonic diagnostic apparatus UL1, the value may be set into the second ultrasonic diagnostic apparatus UL2, which may thereby cause the same value to be set for the preference to be shared between the first ultrasonic diagnostic apparatus UL1 and second ultrasonic diagnostic apparatus UL2.

Therefore, sharing of values of preferences involves two cases: one being the case in which the same value is set for a certain preference, and the other being the case in which the choice as to whether the same value will be set is left to the operator, etc. and there is a possibility that the same value will be set.

Figure 7:
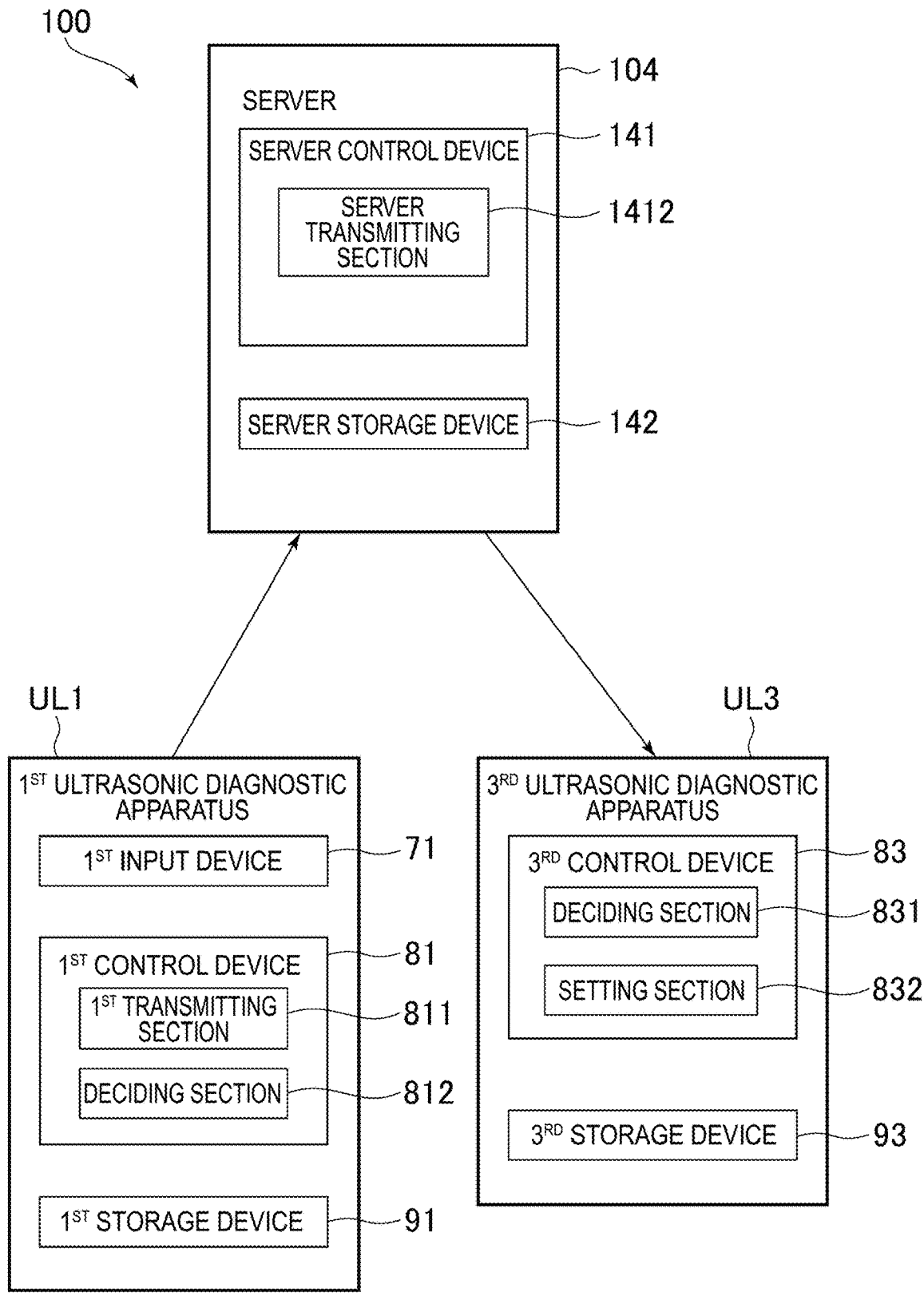
FIG. 7 A block diagram showing the first ultrasonic diagnostic apparatus, a third ultrasonic diagnostic apparatus, and the server in a variation of the first embodiment.

Next, a variation of the first embodiment will be described. In the variation, values of preferences input at the first input device 71 in the first ultrasonic diagnostic apparatus UL1 are transmitted from the first ultrasonic diagnostic apparatus UL1 to a third ultrasonic diagnostic apparatus UL3 via the server 104, as shown in FIG. 7.

The third ultrasonic diagnostic apparatus UL3 is one of the ultrasonic diagnostic apparatuses 101, 102, 103 excluding the first ultrasonic diagnostic apparatus UL1, and at the same time, is an ultrasonic diagnostic apparatus having a possibility of serving as the second ultrasonic diagnostic apparatus UL2 with which values of preferences input at the first ultrasonic diagnostic apparatus UL1 are to be shared.

The control device 8 and storage device 9 in the third ultrasonic diagnostic apparatus UL3 will be referred to herein as a third control device 83 and a third storage device 93, respectively. The server 104 does not have the deciding section 1411, and instead, the third control device 83 has the deciding section 831. Similarly to the second control device 82, the third control device 83 has a setting section 832.

Similarly to the other control devices, the third control device 83 loads programs stored in the third storage device 93, and executes the functions of the deciding section 831 and setting section 832 according to the programs.

The first control device 81 in the first ultrasonic diagnostic apparatus UL1 has a deciding section 812. The first control device 81 loads a program stored in the first storage device 91, and executes the function of the deciding section 812 according to the program.

Now an operation of the variation of the first embodiment will be described based on the flow chart in FIG. 8. Step S11 is similar to Step S1 shown in FIG. 5, the description of which will be omitted. At Step S12, the deciding section 812 in the first ultrasonic diagnostic apparatus UL1 decides whether or not a preference corresponding to the value input at Step S11 is the preference to be shared with the second ultrasonic diagnostic apparatus UL2. In the variation, the deciding section 812 makes said decision based on specification information I1, I2 or I3 shown in FIGS. 9 to 11.

The specification information I1 is stored in the storage device 9 in the ultrasonic diagnostic apparatus 101. When the ultrasonic diagnostic apparatus 101 serves as the first ultrasonic diagnostic apparatus UL1, the deciding section 812 makes said decision based on the specification information I1.

In the specification information I1 is stored any of preferences A, B, C set into the ultrasonic diagnostic apparatus 101 that is to be shared with at least one of the other ultrasonic diagnostic apparatuses 102, 103 (the second ultrasonic diagnostic apparatus UL2). In other words, the specification information I1 specifies any of the preferences set into the ultrasonic diagnostic apparatus 101 for which preference the ultrasonic diagnostic apparatus 101 corresponds to either of the first ultrasonic diagnostic apparatus UL1 or second ultrasonic diagnostic apparatus UL2.

In the specification information I1 shown in FIG. 9, the preference to be shared is preference B. When the value input at Step S11 is a value of preference B, the deciding section 812 decides that it is the preference to be shared with the second ultrasonic diagnostic apparatus UL2.

The specification information I2 is stored in the storage device 9 in the ultrasonic diagnostic apparatus 102. When the ultrasonic diagnostic apparatus 102 serves as the first ultrasonic diagnostic apparatus UL1, the deciding section 812 makes said decision based on the specification information I2.

In the specification information I2 is stored any of preferences A, B, C set into the ultrasonic diagnostic apparatus 102 that is to be shared with at least one of the other ultrasonic diagnostic apparatuses 101, 103 (the second ultrasonic diagnostic apparatus UL2). In other words, the specification information I2 specifies any of the preferences set into the ultrasonic diagnostic apparatus 102 for which preference the ultrasonic diagnostic apparatus 102 corresponds to either the first ultrasonic diagnostic apparatus UL1 or second ultrasonic diagnostic apparatus UL2.

In the specification information I2 shown in FIG. 10, the preferences to be shared are preferences A, B. When the value input at Step S11 is a value of preference A or B, the deciding section 812 decides that it is the preference to be shared with the second ultrasonic diagnostic apparatus UL2.

The specification information I3 is stored in the storage device 9 in the ultrasonic diagnostic apparatus 103. When the ultrasonic diagnostic apparatus 103 serves as the first ultrasonic diagnostic apparatus UL1, the deciding section 812 makes said decision based on the specification information I3.

In the specification information I3 is stored any of preferences A, B, C set into the ultrasonic diagnostic apparatus 103 that is to be shared with at least one of the other ultrasonic diagnostic apparatuses 101, 102 (the second ultrasonic diagnostic apparatus UL1). In other words, the specification information I3 specifies any of the preferences set into the ultrasonic diagnostic apparatus 103 for which preference the ultrasonic diagnostic apparatus 103 corresponds to either of the first ultrasonic diagnostic apparatus UL1 or second ultrasonic diagnostic apparatus UL2.

In the specification information I3 shown in FIG. 11, the preference to be shared is preference A. When the value input at Step S11 is a value of preference A, the deciding section 812 decides that it is the preference to be shared with the second ultrasonic diagnostic apparatus UL2.

Here, the specification information I1 to I3 do not include information for specifying the other ultrasonic diagnostic apparatus with which said preferences A, B, C are to be shared. Specifically, while the specification information I1 specifies preference B to be shared with the ultrasonic diagnostic apparatus(es) other than the ultrasonic diagnostic apparatus 101, it does not specify any ultrasonic diagnostic apparatus with which preference B is to be shared. Similarly, while the specification information I2 specifies preferences A, B to be shared with the ultrasonic diagnostic apparatus (es) other than the ultrasonic diagnostic apparatus 102, it does not specify any ultrasonic diagnostic apparatus with which preferences A, B are to be shared. In addition, while the specification information I3 specifies preference A to be shared with the ultrasonic diagnostic apparatus(es) other than the ultrasonic diagnostic apparatus 103, it does not specify any ultrasonic diagnostic apparatus with which preference A is to be shared.

In the case that the preference corresponding to the value input at Step S11 matches a preference specified in the specification information I1, I2, I3, and it is decided that the preference is the one to be shared with the second ultrasonic diagnostic apparatus UL2 ("YES" at Step S12), the flow goes to the processing at Step S13. On the other hand, in the case that the preference corresponding to the value input at Step S11 does not match the preference specified in the specification information I1, I2, I3, and it is decided that the preference is the one not to be shared with the second ultrasonic diagnostic apparatus UL2 ("NO" at Step S12), the processing is terminated.

Step S13 is similar to Step S2 shown in FIG. 5, the description of which will be omitted. At Step S14, the transmitting section 1412 in the server 104 transmits the values of the preferences input at Step S1 and transmitted to the server 104 at Step S13. The transmitting section 1412 performs said transmission to the third ultrasonic diagnostic apparatus UL3 via the network 105. The third ultrasonic diagnostic apparatus UL3 is one of the ultrasonic diagnostic apparatuses 101, 102, 103 excluding the first ultrasonic diagnostic apparatus UL1 as described above, i.e., excluding the ultrasonic diagnostic apparatus at which said input is performed at Step S11.

Next, at Step S15, the deciding section 831 in the third ultrasonic diagnostic apparatus UL3 decides whether or not the preference corresponding to said value transmitted from the transmitting section 1412 at Step S13 is the preference to be shared with the first ultrasonic diagnostic apparatus UL1, and decides whether or not the third ultrasonic diagnostic apparatus UL3 corresponds to the second medical image capture apparatus UL2. This decision is to decide whether or not the preference corresponding to said value transmitted from the transmitting section 1412 is the preference to be shared between the first ultrasonic diagnostic apparatus UL1 and second ultrasonic diagnostic apparatus.

In the case that the ultrasonic diagnostic apparatus 101 is not the first ultrasonic diagnostic apparatus UL1 and is the third ultrasonic diagnostic apparatus UL3, the value of said preference is transmitted to the ultrasonic diagnostic apparatus 101 from the server 104. The deciding section 831 in the ultrasonic diagnostic apparatus 101 makes the aforementioned decision, i.e., a decision as to whether or not the ultrasonic diagnostic apparatus 101 corresponds to the second ultrasonic diagnostic apparatus UL2 based on the specification information I1. When the value of the preference transmitted from the server 104 is a value of preference B, the ultrasonic diagnostic apparatus 101 corresponds to the second ultrasonic diagnostic apparatus UL2.

In the case that the ultrasonic diagnostic apparatus 102 is not the first ultrasonic diagnostic apparatus UL1 and is the third ultrasonic diagnostic apparatus UL3, the value of said preference is transmitted to the ultrasonic diagnostic apparatus 102 from the server 104. The deciding section 831 in the ultrasonic diagnostic apparatus 102 makes the aforementioned decision, i.e., a decision as to whether or not the ultrasonic diagnostic apparatus 102 corresponds to the second ultrasonic diagnostic apparatus UL2 based on the specification information I2. When the value of the preference transmitted from the server 104 is a value of preference A, B, the ultrasonic diagnostic apparatus 102 corresponds to the second ultrasonic diagnostic apparatus UL2.

In the case that the ultrasonic diagnostic apparatus 103 is not the first ultrasonic diagnostic apparatus UL1 and is the third ultrasonic diagnostic apparatus UL3, the value of said preference is transmitted to the ultrasonic diagnostic apparatus 103 from the server 104. The deciding section 831 in the ultrasonic diagnostic apparatus 103 makes the aforementioned decision, i.e., a decision as to whether or not the ultrasonic diagnostic apparatus 103 corresponds to the second ultrasonic diagnostic apparatus UL2 based on the specification information I3. When the value of the preference transmitted from the server 104 is a value of preference A, the ultrasonic diagnostic apparatus 103 corresponds to the second ultrasonic diagnostic apparatus UL2.

As described above, in the case that the preference transmitted from the server 104 matches a preference specified in the specification information I1, I2, I3 stored in the respective ultrasonic diagnostic apparatuses 101, 102, 103, the deciding section 831 decides that the third ultrasonic diagnostic apparatus UL3 corresponds to the second ultrasonic diagnostic apparatus UL2. On the other hand, in the case that the preference transmitted from the server 104 does not match a preference specified in the specification information I1, I2, I3 stored in the respective ultrasonic diagnostic apparatuses 101, 102, 103, the deciding section 831 decides that the third ultrasonic diagnostic apparatus UL3 does not correspond to the second ultrasonic diagnostic apparatus UL2.

In the case that the deciding section 831 has decided that the third ultrasonic diagnostic apparatus UL3 does not correspond to the second medical image capture apparatus UL2 ("NO" at Step S15), the processing is terminated. On the other hand, in the case that the deciding section 831 decides that the third ultrasonic diagnostic apparatus UL3 corresponds to the second medical image capture apparatus UL2 ("YES" at Step S15), the flow goes to the processing at Step S16. At Step S16, similarly to Step S5, the setting section 832 (setting section 822) in the third ultrasonic diagnostic apparatus UL3 decided to correspond to the second ultrasonic diagnostic apparatus UL2 stores the values of the preferences transmitted from the server 104 in the third storage device 93 (the second storage device 92). For example, in the case that the third ultrasonic diagnostic apparatus UL3 is the ultrasonic diagnostic apparatus 101, and it is decided that the ultrasonic diagnostic apparatus 101 corresponds to the second ultrasonic diagnostic apparatus UL2, the value of the preference transmitted from the server 104 is stored in the storage device 9 (the third storage device 93, the second storage device 92) in the ultrasonic diagnostic apparatus 101.

Next, a second embodiment will be described. In the following description, details of similar matters to those in the first embodiment will be omitted.

A system 100 in the present embodiment has a similar configuration to that shown in FIG. 1. The ultrasonic diagnostic apparatuses 101, 102, 103 also have the configuration shown in FIG. 2. In the present embodiment, however, the ultrasonic diagnostic apparatuses 101, 102, 103 share all preferences A, B, C among them, as shown in FIG. 12.

Figure 12:
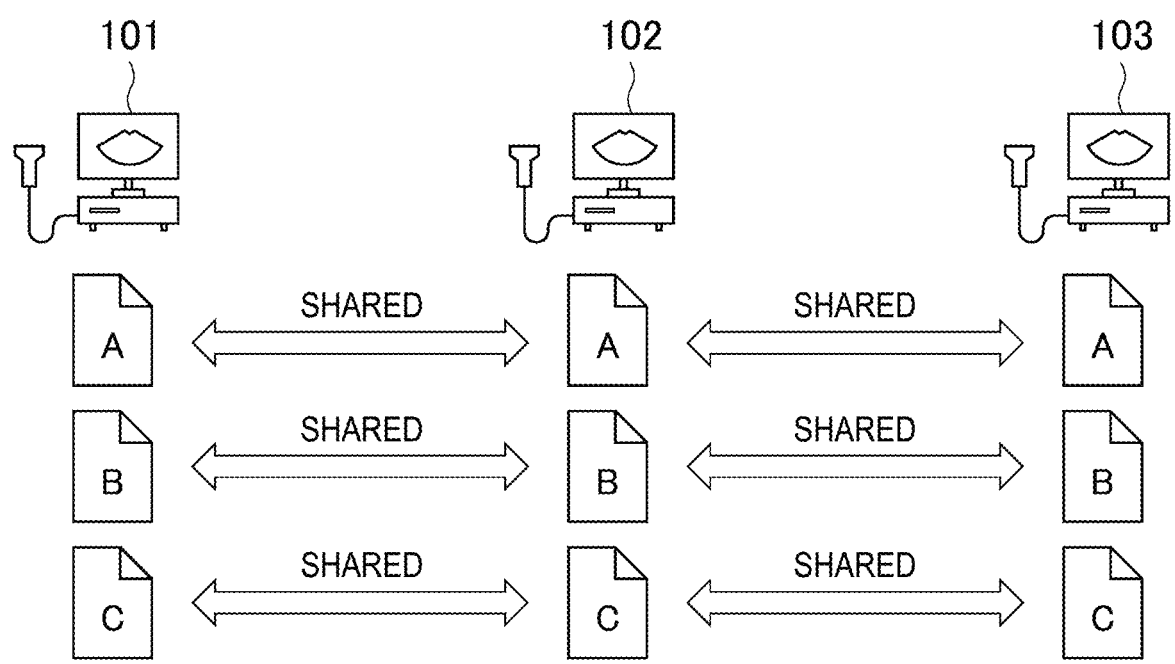
FIG. 12 A diagram explaining preferences set in each of the plurality of ultrasonic diagnostic apparatuses in a second embodiment.

Although only three preferences A, B, C are shown in FIG. 12, they are only some of preferences to be set into the ultrasonic diagnostic apparatuses 101, 102, 103. In the present embodiment, three or more preferences are set into the ultrasonic diagnostic apparatuses 101, 102, 103, as will be discussed later.

Figure 13:
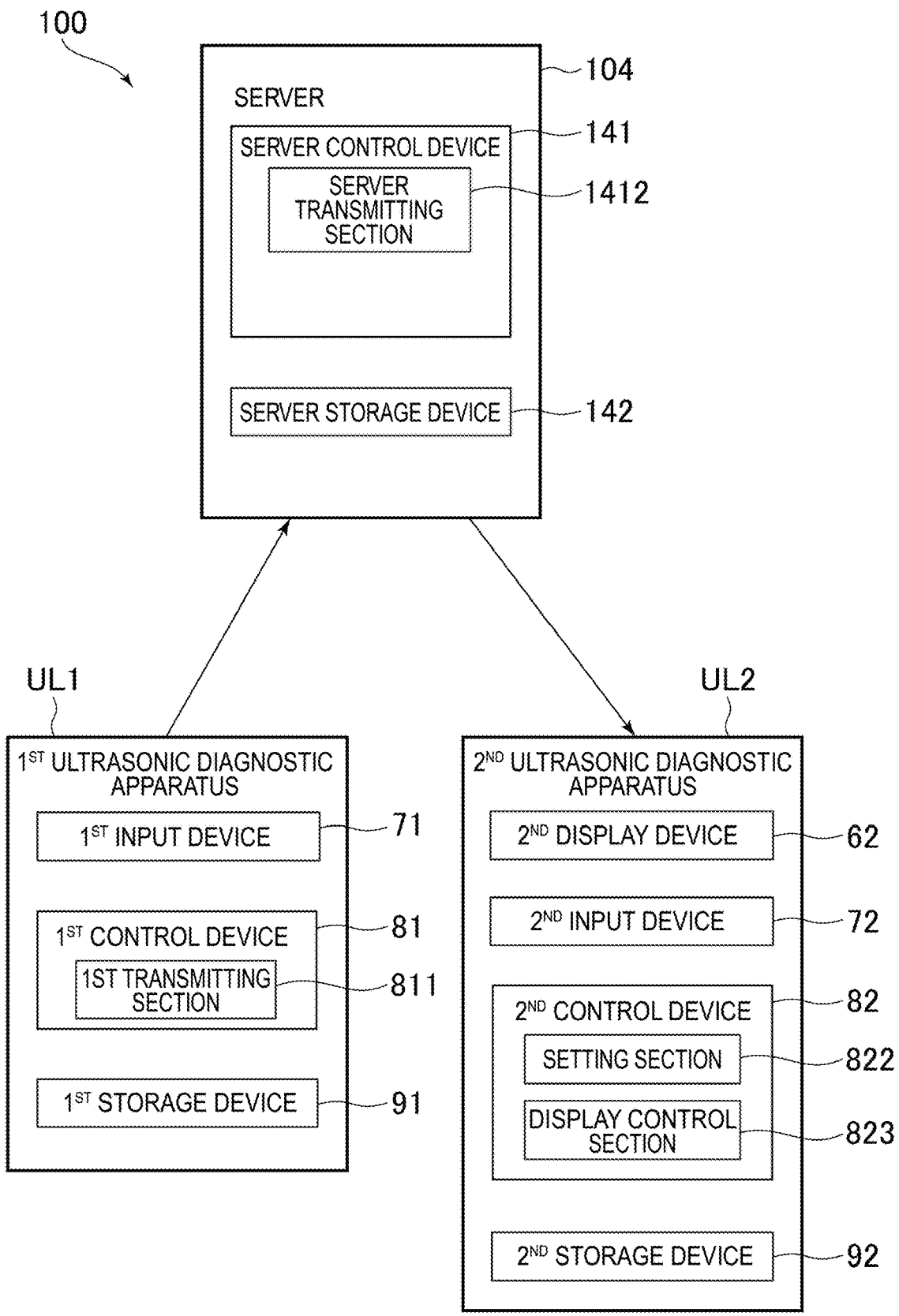
FIG. 13 A block diagram showing the first ultrasonic diagnostic apparatus, second ultrasonic diagnostic apparatus, and server in the second embodiment.

In the present embodiment, again, the system 100 has the first ultrasonic diagnostic apparatus UL1 and second ultrasonic diagnostic apparatus UL2, as shown in FIG. 13. In the present embodiment, the first ultrasonic diagnostic apparatus UL1 and second ultrasonic diagnostic apparatus UL2 are ultrasonic diagnostic apparatuses sharing therebetween preferences in the plurality of ultrasonic diagnostic apparatuses 101, 102, 103. Similarly to the first embodiment, the first ultrasonic diagnostic apparatus UL1 is one of the plurality of ultrasonic diagnostic apparatuses 101, 102, 103 at which apparatus an input of values of preferences is performed. The second ultrasonic diagnostic apparatus UL2 is an ultrasonic diagnostic apparatus into which apparatus the values of the preferences input at the first ultrasonic diagnostic apparatus UL1 are set. Since in the present embodiment, preferences are shared among all the ultrasonic diagnostic apparatuses 101, 102, 103, those of the ultrasonic diagnostic apparatuses 101, 102, 103 other than the one corresponding to the first ultrasonic diagnostic apparatus UL1 correspond to the second ultrasonic diagnostic apparatus UL2. Therefore, the second ultrasonic diagnostic apparatus UL2 includes a plurality of ultrasonic diagnostic apparatuses.

Components in FIG. 13 designated by the same symbols as those in FIG. 4 have the same configuration as that in FIG. 4. In the present embodiment, the server 104 does not have the deciding section 1411, as shown in FIG. 13.

In the present embodiment, the display device 6 and input device 7 in the second ultrasonic diagnostic apparatus UL2 are referred to as a second display device 62 and a second input device 72, respectively. The second ultrasonic diagnostic apparatus UL2 has a display control section 823. The second control device 82 loads a program stored in the second storage device 92, and causes the function of the display control section 823 to be executed according to the program. This will be discussed in detail later.

On the second display device 62 is displayed a notification window, described below, by the display control section 823. This will be discussed in detail later. The second display device 62 is an exemplary embodiment of the display device in the present invention. The second input device 72 is an exemplary embodiment of the second input device in the present invention.

In the first storage device 91 and second storage device 92 are stored the same value for each preference to be shared. In the first storage device 91 and second storage device 92 is stored a data file consisting of values of preferences located in a folder representing a category, which will be discussed later. The preferences will be discussed in detail later.

Figure 14:
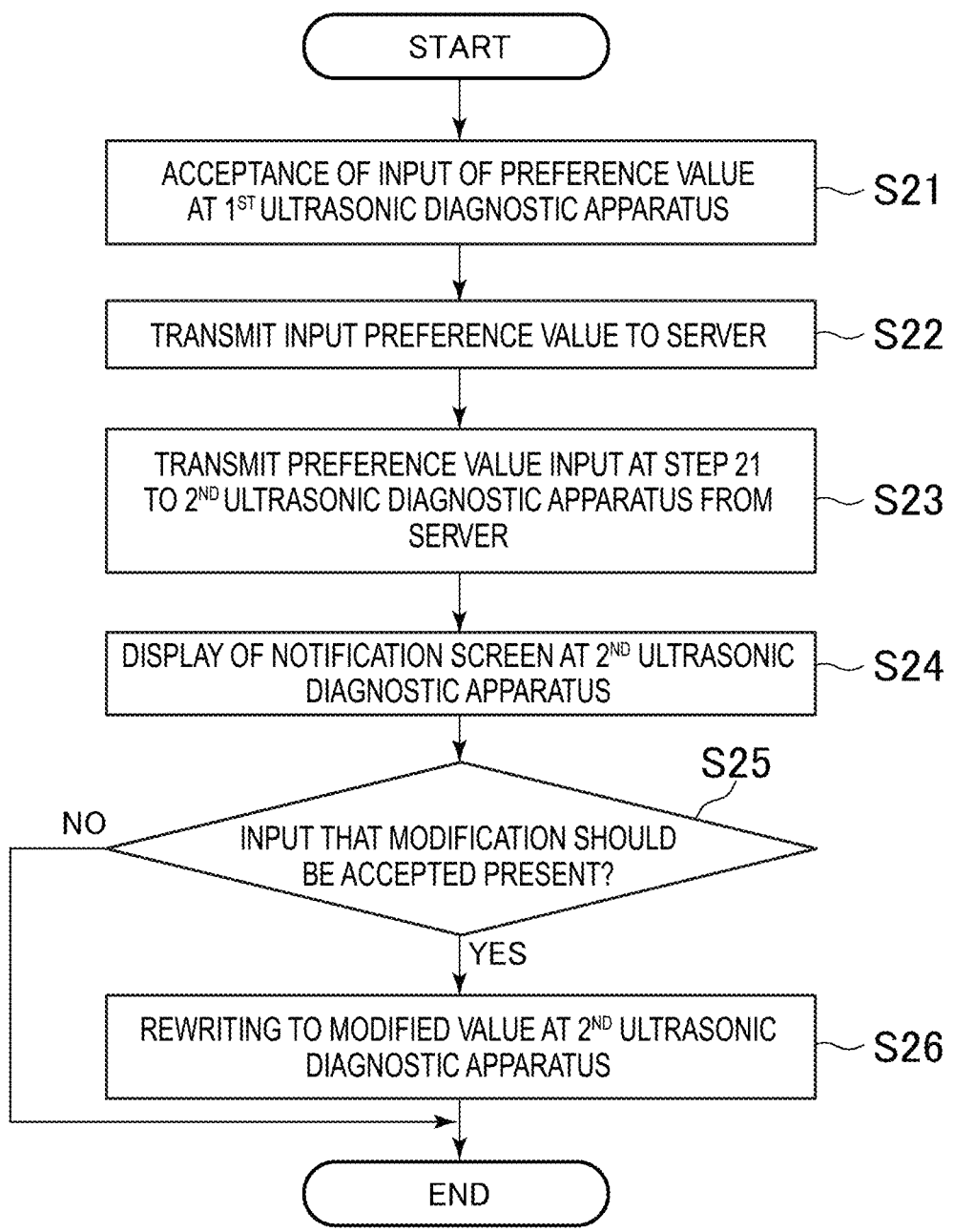
FIG. 14 A flow chart showing an operation of the second embodiment.

Now an operation of the present embodiment will be described based on the flow chart in FIG. 14. The flow chart in FIG. 14 represents a flow showing processing when setting a value of a preference input at the first ultrasonic diagnostic apparatus UL1 as a value of the preference in the second ultrasonic diagnostic apparatus UL2.

Figure 8:
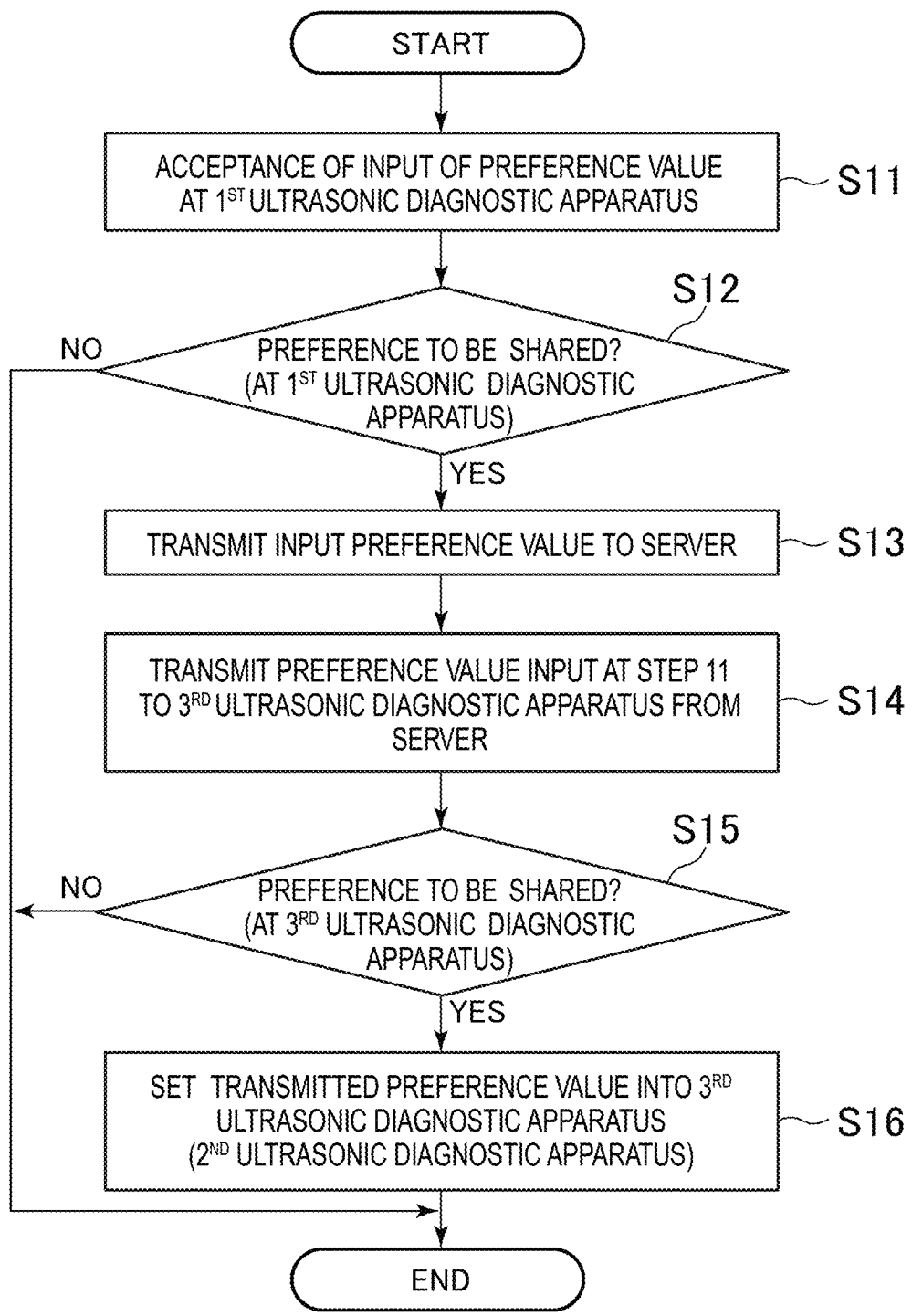
FIG. 8 A flow chart showing an operation of the variation of the first embodiment.

Steps S21, S22 are similar to Steps S1, S2 shown in FIG. 5 and Steps S11, S13 shown in FIG. 8. At Step S21, however, the first input device 71 accepts an input of modifying the value of said preference to be shared stored in the first storage device 91. The value of the preference input at Step S21 will be referred to herein as a modified value. At Step S22, the modified value is transmitted to the server.

At Step S23, the transmitting section 1412 in the server 104 transmits the modified value input at Step S21 and transmitted to the server 104 at Step S22, to the second ultrasonic diagnostic apparatus UL2 via the network 105. The second ultrasonic diagnostic apparatus UL2 is one of the ultrasonic diagnostic apparatuses 101, 102, 103 excluding that at which the input is performed at Step S21.

Figure 15:
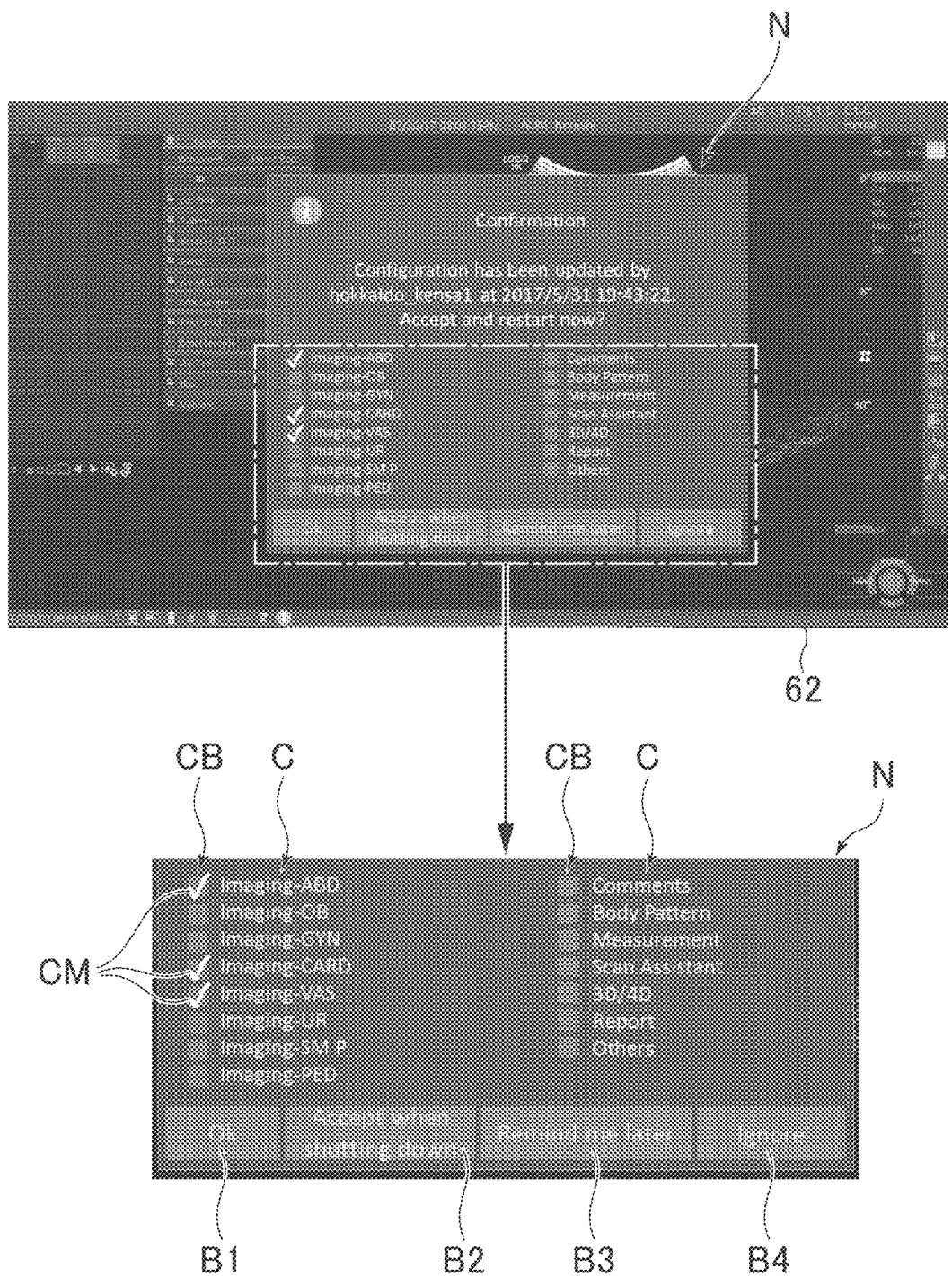
FIG. 15 A diagram showing an example of a notification window displayed on a second display device.

Next, at Step 24, the display control section 823 displays a notification window N on the second display device 62, as shown in FIG. 15. The notification window N is for notifying the preference to which the modified value transmitted to the second ultrasonic diagnostic apparatus UL2 at Step S23 pertains. The notification window N is displayed during capture of an ultrasonic image in the second ultrasonic diagnostic apparatus UL2.

Now the notification window N will be described in detail. The notification window N includes characters C designating each of a plurality of preferences to be set in the ultrasonic diagnostic apparatuses 101, 102, 103, and a check box CB laid on the left side of the characters C. The notification window N also has first to fourth buttons B1 to B4. The first to fourth buttons B1 to B4 in the notification window N will be discussed later.

The characters C specifically designate preferences of imaging conditions, a preference of a comment, a preference of a body pattern, a preference of measurement, a preference of a reconstruction condition, etc. For example, preferences including imaging conditions are designated by characters "Imaging-ABD," "Imaging-CARD," "Imaging-VAS," and the like, where the preference is represented by the characters "'Imaging" plus characters "ABD," "CARD," or "VAS" indicating a body part to be imaged of the subject. Moreover, there are eight preferences including imaging conditions in these "ABD," "CARD," and "VAS" examples, which are separately assigned to body parts. Note that "ABD" represents an abdomen, "CARD" represents a heart, and "VAS" represents a blood vessel.

The preference of a comment is designated by characters "Comments," and the preference of a body pattern is designated by characters "Body Pattern". The preference of measurement is designated by characters "Measurement," and the preference of a reconstruction condition is designated by characters "3D/4D." Although in FIG. 15, other characters are also displayed as the preferences, the description thereof will be omitted here. Moreover, the preferences included in the notification window N are merely exemplary, and the preferences are not limited thereto in the present invention.

In the check box CB corresponding to the preference to which the modified value input at Step S21 pertains, a check mark CM is displayed.

Here, the preferences are classified into categories that make it possible to decide whether or not said modified value affects capture of an ultrasonic image. For example, although there are a large number of parameters included in imaging conditions, the imaging conditions are classified for each body part to be imaged of the subject. Referring to FIG. 15, check marks CM are displayed at check boxes CB corresponding to "Imaging-ABD," "Imaging-CARD," and "Imaging-VAS." When image capture is performed on a body part to be imaged other than the abdomen, heart, and blood vessel, the operator is able to decide that the modified value input at the first ultrasonic diagnostic apparatus UL1 at Step S21 does not relate to image capture currently running at the second ultrasonic diagnostic apparatus UL2. Thus, preferences classified into categories that make it possible to decide whether or not said modified value affects capture of an ultrasonic image are displayed in the notification window N, and a check mark CM is displayed at a preference to which the modified value pertains, whereby the operator can easily decide whether or not the modified value relates to currently running image capture.

Now the first to fourth buttons B1 to B4 in the notification window N will be described. The button B1 has characters "Ok," and the button B2 has characters "Accept when shutting down." The button B3 has characters "Remind me later," and the button B4 has characters "Ignore."

The button B1 is for accepting an input by the operator who accepts the modified value input at the first input device 71 at Step S21, and directs the value to be set into the second ultrasonic diagnostic apparatus UL2. Upon clicking-on of the button B1, said modified value is set at once.

The button B2 is for accepting an input by the operator who accepts the modified value input at the first input device 71 at Step S21, but rather than setting the modified value into the second ultrasonic diagnostic apparatus UL2 at once, directs the modified value to be set immediately before shutting down the second ultrasonic diagnostic apparatus UL2.

The button B3 is for accepting an input by the operator for directing the notification window N to be displayed again later. A required time when to display the notification window N again may be stored in the second storage device 92.

The button B4 is for accepting an input by the operator who does not accept the modified value input at the first input device 71 at Step S21, and directs the modified value not to be set into the second ultrasonic diagnostic apparatus UL2.

By the operator clicking on one of the buttons B1 to B4 using the second input device 72, the input of the direction described above is accepted.

After the notification window N has been displayed at Step S24, the operator clicks on any one of the buttons B1 to B4 using the second input device 72 at Step S25. The setting section 82 decides which of the buttons B1 to B4 has been clicked on. This causes a decision to be made at Step S25 as to whether or not an input for accepting the modified value input at the first input device 71 at Step S21 has been performed.

In the case that the setting section 82 decides that the button B1 or B2 has been clicked on ("YES" at Step S25), the flow goes to the processing at Step S26. On the other hand, in the case that the setting section 82 decides that the button B3 or B4 has been clicked on ("NO" at Step S25), the processing is terminated.

At Step S26, the setting section 82 executes a rewriting function of rewriting a value stored in the second storage device 92 for the preference whose value has been modified at the first input device 71 at Step S21, with said modified value. Here, the time of execution of the rewriting function is different between the case in which the button B1 is clicked on and the case in which the button B2 is clicked on. In the case that the button B1 is clicked on, the setting section 82 executes the rewriting function as soon as the button B1 is clicked on. On the other hand, in the case that the button B2 is clicked on, the setting section 82 executes the rewriting function after completing the capture of an ultrasonic image at the second ultrasonic diagnostic apparatus UL2 and immediately before shutting down the second ultrasonic diagnostic apparatus UL2. In the latter case, for the preference whose value has been modified at the first input device 71 at Step S21, the setting section 82 may store, in addition to the the value stored in the second storage device 92, the modified value input at the first input device 71 at Step S21 into the second storage device 92 (the storing function). In executing the rewriting function, the setting section 82 loads the modified value stored in the second storage device 92 and performs rewriting. The clicking-on of the button B2 is an exemplary embodiment of the input for pending setting in the present invention. The storing function by the setting section 82 is an exemplary embodiment of the storing function in the present invention. The time at which the rewriting function is executed when the button B2 is clicked on, i.e., the time after completion of image capture and immediately before shutting down the second ultrasonic diagnostic apparatus UL2, is an exemplary embodiment of the required time in the present invention.

Now the alternative case in which the setting section 82 decides that the button B3 or B4 has been clicked on ("NO" at Step S25) and the processing is terminated will be described. In the case that the button B3 is clicked on, although the processing is terminated for the present, the notification window N is displayed again at the required time. In this case, for the preference whose value has been modified at the first input device 71 at Step S21, the modified value input at the first input device 71 at Step S21 may be stored in the second storage device 92, in addition to the value stored in the second storage device 92. The display control section 823 loads the modified value stored in the second storage device 92, and displays the notification window N again.

Next, a variation of the second embodiment will be described. In the second embodiment, again, similarly to the first embodiment, some of a plurality of preferences may be shared between the first ultrasonic diagnostic apparatus UL1 and second ultrasonic diagnostic apparatus UL2. For example, preferences A, B, C may be shared among the ultrasonic diagnostic apparatuses 101, 102, 103 in the conditions shown in FIG. 3, instead of those shown in FIG. 12.

Figure 16:
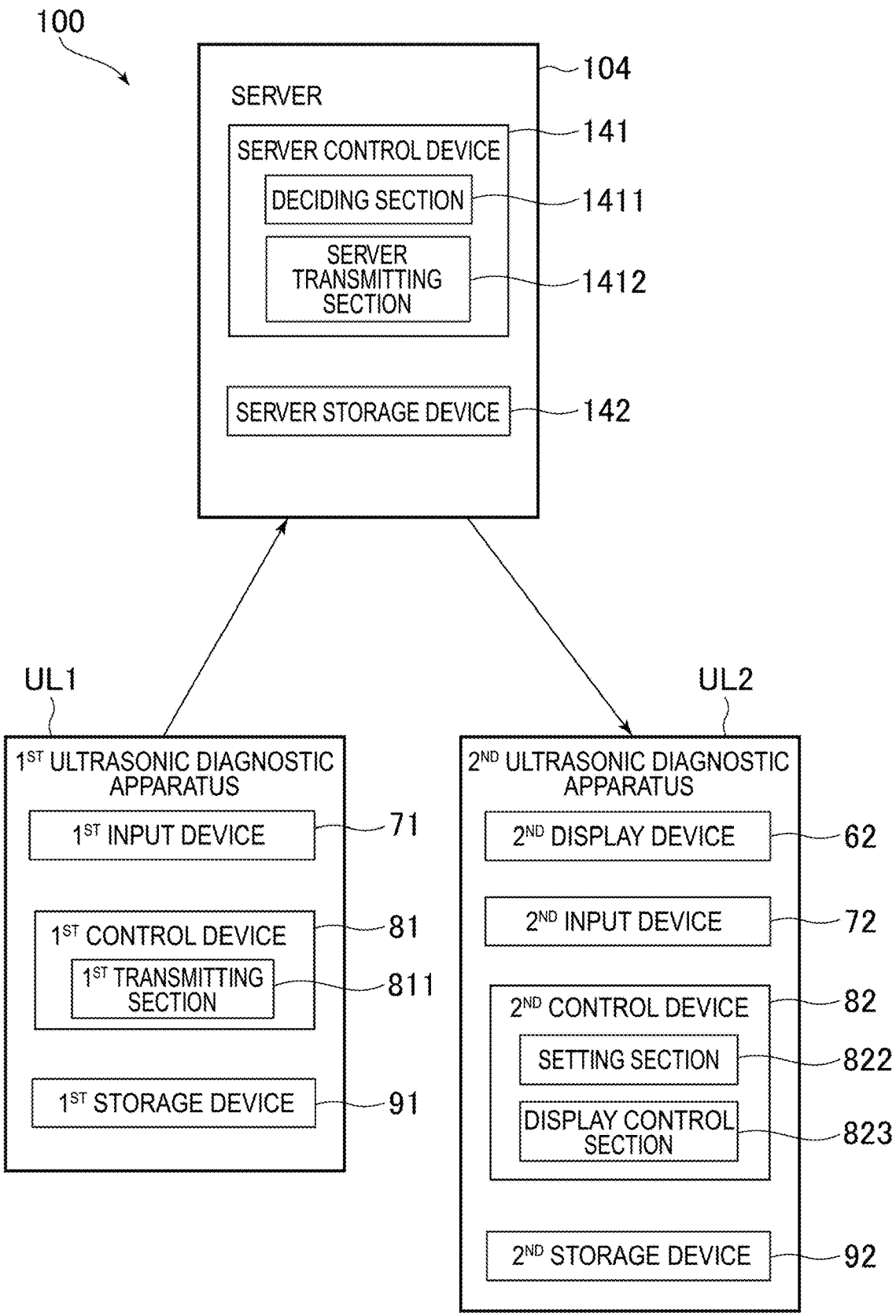
FIG. 16 A block diagram showing the first ultrasonic diagnostic apparatus, second ultrasonic diagnostic apparatus, and server in a first variation of the second embodiment.

First, a first variation of the second embodiment will be described. In the system 100 in the first variation shown in FIG. 16, the server 104 has the deciding section 1411. Other components are similar to those in FIG. 13.

Figure 17:
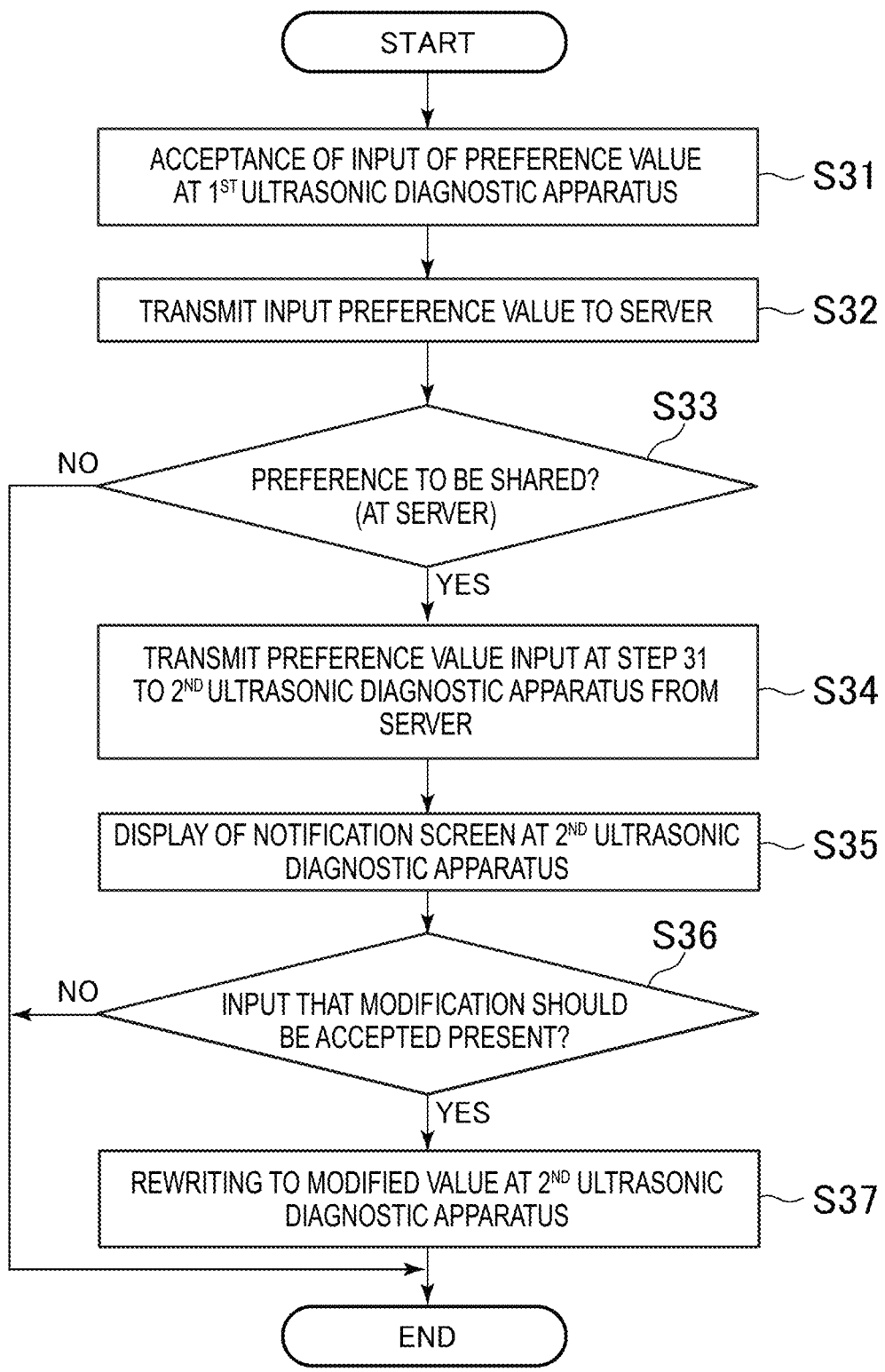
FIG. 17 A flow chart showing an operation of the first variation of the second embodiment.

Now an operation of the present embodiment will be described based on the flow chart in FIG. 17. The processing at Steps S31, S32 is similar to that at Steps S21, S22 shown in FIG. 14. The processing at Step S33 is similar to that at Step S3 shown in FIG. 5. The processing at Steps S34 to S37 is similar to that at Steps S23 to S26 shown in FIG. 14.

Figure 18:
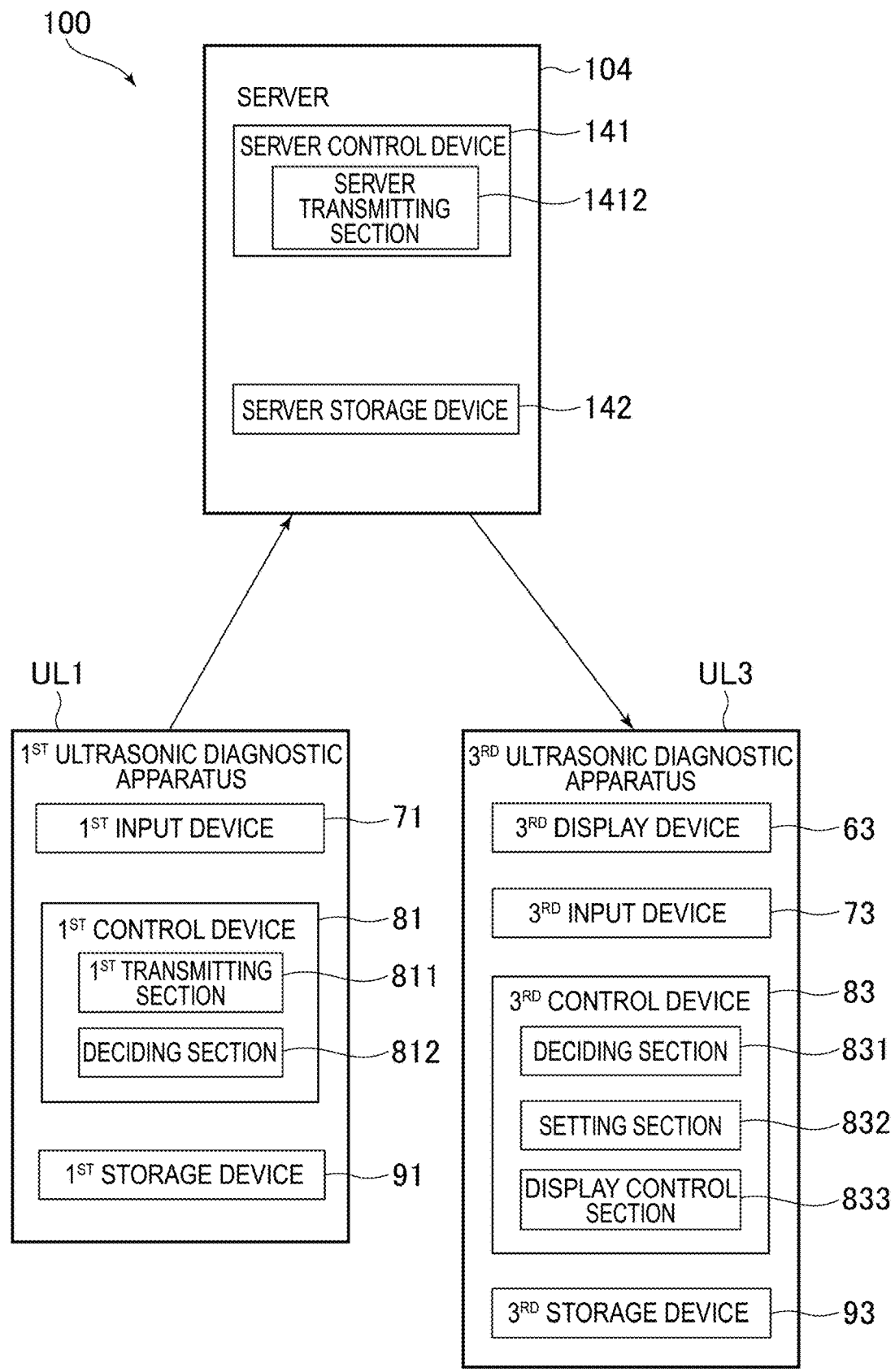
FIG. 18 A block diagram showing the first ultrasonic diagnostic apparatus, second ultrasonic diagnostic apparatus, and server in a second variation of the second embodiment.

Next, a second variation will be described. The system 100 in the second variation shown in FIG. 18 has the third ultrasonic diagnostic apparatus UL3 in place of the second ultrasonic diagnostic apparatus UL2 shown in FIG. 13. The third ultrasonic diagnostic apparatus UL3 also includes a plurality of ultrasonic diagnostic apparatuses.

Moreover, the third ultrasonic diagnostic apparatus UL3 has a third display device 63, a third input device 73, a third control device 83, and a third storage device 93, in place of the second display device 62, second input device 72, second control device 82, and second storage device 92. The third display device 63, third input device 73, and third storage device 93 are configured similarly to the second display device 62, second input device 72, and second storage device 92. The functions of the setting section 832 and display control section 833 in the third control device 83 are similar to those of the setting section 822 and display control section 823 in the the second control device 82. Moreover, the third control device 83 executes the function of the deciding section 831, similarly to the third control device 83 shown in FIG. 7.

The first control device 81 in the first ultrasonic diagnostic apparatus UL1 has the deciding section 812 similarly to the variation of the first embodiment.

Now an operation of the present embodiment will be described based on the flow chart in FIG. 19. The processing at Step S41 is similar to that at Step S21 shown in FIG. 14. The processing at Steps S42 to S45 is similar to that at Steps S12 to 15 shown in FIG. 8. The processing at Steps S46 to S48 is similar to that at Steps S24 to S26 in FIG. 14. Specifically, at Step S46, the notification window N is displayed in the third ultrasonic diagnostic apparatus UL3 decided to correspond to the second ultrasonic diagnostic apparatus UL2 at Step S44. Then, once an input of accepting said modified value has been performed at Step S47 in the third ultrasonic diagnostic apparatus UL3 in which the notification window N is displayed, execution of said rewriting function is effected in the third ultrasonic diagnostic apparatus UL3 at Step S48.

While the present invention has been described with reference to the embodiments above, it will be easily recognized that the present invention may be practiced with several modifications without departing from the scope and spirit thereof. For example, in the embodiments above, the medical image capture apparatus is exemplified by the ultrasonic diagnostic apparatus; however, the medical image capture apparatus in the present invention is not limited to the ultrasonic diagnostic apparatus. For example, the present invention may be similarly applied to medical image capture apparatuses, such as an X-ray CT apparatus and/or an MRI apparatus.

Moreover, in the first embodiment, the second ultrasonic diagnostic apparatus UL2 may include a plurality of ultrasonic diagnostic apparatuses.

Furthermore, when the button B2 is clicked on in the second embodiment, immediately before shutting down the second ultrasonic diagnostic apparatus UL2, an icon (not shown) indicating that said modified value to be used in rewriting by said rewriting function is stored in the second storage device 92 may be displayed by the display control section 823 on the the second display device 62 in the second ultrasonic diagnostic apparatus UL2 in use. Likewise, when the button B3 is clicked on, in the meantime until the notification window N is displayed again, an icon (not shown) indicating that said modified value is stored in the second storage device 92 may be displayed by the display control section 823 on the the second display device 62 in the second ultrasonic diagnostic apparatus UL2 in use.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

We claim:

1. A system comprising a plurality of medical image capture apparatuses each having an input device for accepting an input by an operator, said plurality of medical image capture apparatuses being connected via a network, and including a first medical image capture apparatus and a second medical image capture apparatus sharing between them some of a plurality of preferences set in each of said plurality of medical image capture apparatuses, said system comprising:
    a storage device in which specification information is stored, said specification information specifying some of the plurality of preferences set in each of said plurality of medical image capture apparatuses that are to be shared between said first and second medical image capture apparatuses;
    at least one control device, said control device executing:
    a deciding function of deciding, once said input device in said first medical image capture apparatus has accepted an input of a value of at least one of said plurality of preferences set in the first medical image capture apparatus, whether or not a preference corresponding to said input value is to be shared between said first and second medical image capture apparatuses based on said specification information; and
    a setting function of setting, in a case that said preference is decided by said deciding function to be shared, the value of said preference into said second medical image capture apparatus.

2. The system as recited in claim 1, wherein:
    the decision by said deciding function includes identification of said second medical image capture apparatus with which said preference corresponding to said input value is to be shared,
    said control device further executes a transmitting function of transmitting the value of said preference to said second medical image capture apparatus identified by said deciding function, and
    said setting function stores the value of said preference transmitted by the transmitting function into the storage device in said second medical image capture apparatus.

3. The system as recited in claim 2, comprising:
    a server connected with said plurality of medical image capture apparatuses via said network, wherein
    said control device is comprised of a plurality of control devices,
    said server has said storage device, and a server control device for executing said deciding function and said transmitting function,
    said second medical image capture apparatus has a second control device for executing said setting function, and
    said plurality of control devices are configured to include said server control device and said second control device.

4. The system as recited in claim 3, wherein: said specification information specifies preferences to be shared between said first and second medical image capture apparatuses for each of said plurality of medical image capture apparatuses.

5. The system as recited in claim 4, wherein: in a case that said preference corresponding to the value input at said first medical image capture apparatus is defined in said specification information as a preference to be shared in both said first and second ultrasonic diagnostic apparatuses, the deciding function in said server decides that said preference is to be shared between said first and second ultrasonic diagnostic apparatuses.

6. The system as recited in claim 3, wherein:
    said first medical image capture apparatus has a first control device for executing a first transmitting function of transmitting the value of said preference accepted at said input device to said server via said network, and
    said deciding function in said server is configured to make said decision on said preference corresponding to said value output to said network and input to said server by said first transmitting function.

7. The system as recited in claim 1, wherein: a third medical image capture apparatus that is one of said plurality of medical image capture apparatuses excluding said first medical image capture apparatus has said storage device and said control device.

8. The system as recited in claim 7, comprising:
    a server connected with said plurality of medical image capture apparatuses via said network, wherein
    said first medical image capture apparatus has a first control device for executing a first transmitting function of transmitting the value of said preference accepted at said input device to said server via said network,
    said server has a server control device for executing a server transmitting function of transmitting to said third medical image capture apparatus via said network the value of said preference transmitted to said server by said first transmitting function,
    said deciding function in said control device in said third medical image capture apparatus comprises deciding whether or not said preference corresponding to said input value is to be shared with said first medical image capture apparatus, and deciding whether or not said third medical image capture apparatus corresponds to said second medical image capture apparatus, and
    in a case that said third medical image capture apparatus is decided to correspond to said second medical image capture apparatus, said setting function in said control device in said third medical image capture apparatus performs said setting on said third medical image capture apparatus decided to correspond to said second medical image capture apparatus.

9. The system as recited in claim 7, wherein: said specification information specifies a preference to be shared with said first medical image capture apparatus among those set into a medical image capture apparatus in which said specification information is stored, and yet does not contain information that identifies said first medical image capture apparatus with which said preference is to be shared.

10. The system as recited in claim 9, wherein: in a case that said preference corresponding to the value input at said first medical image capture apparatus matches said preference specified in said specification information, said deciding function in each of said plurality of medical image capture apparatuses decides that said preference is a to be shared between said first and second ultrasonic diagnostic apparatuses.

11. The system as recited in claim 8, wherein:
said first medical image capture apparatus has said storage device,
said first control device further executes said deciding function based on said specification information stored in said storage device in said first medical image capture apparatus, and
in a case that a preference is decided to be shared by said deciding function, said first transmitting function performs said transmission.

12. A system comprising a plurality of medical image capture apparatuses connected with one another via a network, wherein
at least some of said plurality of medical image capture apparatuses include a first medical image capture apparatus and a second medical image capture apparatus sharing between them values of at least some of a plurality of preferences set in each of said medical image capture apparatuses,
said first medical image capture apparatus has a first storage device, a first input device, and a first control device,
said second medical image capture apparatus has a second storage device and a display device,
in said first and second storage devices are stored the values of the at least some of a plurality of preferences to be shared,
said first input device is configured to accept an input for modifying at least one of the values of the at least one of a plurality of preferences to be shared stored in said storage device in said first medical image capture apparatus,
said first control device is configured to execute, once said first input device has accepted the input for modifying at least one of the values of the at least one of the plurality of preferences, a first transmitting function of transmitting the input modified value to said network,
said display device is configured to display, during capture of a medical image in said second medical image capture apparatus, a notification window for notifying said preference to which said input modified value pertains, and
said preference is classified into a category that makes it possible to decide whether or not said input modified value affects the capture of said medical image.

13. The system as recited in claim 12, wherein:
said second medical image capture apparatus has a second input device and a second control device,
said second input device is configured to accept an input for setting said modified value input at said first input device into said second medical image capture apparatus, and
said second control device is configured to execute, once said second input device has accepted said input, a rewriting function of rewriting a value stored in said second storage device for said preference whose value has been modified at said first input device, with said modified value.

14. The system as recited in claim 12, wherein:
said second medical image capture apparatus has a second input device and a second control device,
said second input device is configured to accept an input for pending setting of said modified value input at said first input device into said second medical image capture apparatus, and
said second control device is configured to execute, once said second input device has accepted said input, a storing function of storing, for said preference whose value has been modified at said first input device, said modified value into said second storage device in addition to a value stored in said second storage device.

15. The system as recited in claim 14, wherein: said second control device is configured to execute a rewriting function of rewriting, for said preference whose value has been modified at said first input device, the value stored in said second storage device with said modified value stored in said second storage device at a required time after completion of image capture in said second medical image capture apparatus.

16. The system as recited in claim 14, wherein: said display device displays said notification window again at a required time after said input of pending setting at said second input device, based on the value stored in said second storage device for said preference whose value has been modified at said first input device.

17. The system as recited in claim 11, wherein: a data file consisting of the values of said preferences is stored in said first and second storage devices, said data file being located in a folder representing said category.

18. The system as recited in claim 1, wherein: said preferences are information used for an operation of a medical image capture apparatus.

19. The system as recited in claim 18, wherein: said preferences include imaging conditions for acquiring a medical image in said medical image capture apparatus, information given to said medical image, information used for performing measurement on said medical image, and reconstruction conditions for performing image reconstruction based on data of said medical image.

* * * * *